United States Patent [19]
Lee et al.

[11] Patent Number: 6,051,396
[45] Date of Patent: Apr. 18, 2000

[54] METHOD FOR PRODUCING RETINOBLASTOMA GENE PROTEIN PRODUCTS

[75] Inventors: Wen-Hwa Lee; Eva Y.-H. P. Lee, both of San Diego, Calif.

[73] Assignee: The Regents of the University of California, Oakland, Calif.

[21] Appl. No.: 08/058,784

[22] Filed: May 7, 1993

Related U.S. Application Data

[63] Continuation-in-part of application No. 07/091,547, Aug. 31, 1987, Pat. No. 5,011,773, application No. 07/098,612, Sep. 17, 1987, Pat. No. 4,942,123, application No. 07/108,748, Oct. 15, 1987, abandoned, and application No. 07/265,829, Oct. 31, 1988, abandoned, and a continuation of application No. 07/906,008, Jun. 26, 1992, abandoned, which is a continuation of application No. 07/553,905, Jul. 16, 1990, abandoned.

[51] Int. Cl.[7] .............................. C12N 15/00; C12N 5/00; C12P 21/06; C12P 21/04
[52] U.S. Cl. .................. 435/69.1; 435/172.3; 435/240.2; 435/70.3
[58] Field of Search .............................. 435/69.1, 172.3, 435/240.2

[56] References Cited

U.S. PATENT DOCUMENTS 4,745,051  5/1988  Smith et al. .............................. 435/68

OTHER PUBLICATIONS

Lee, W.–H. et al., "The Retinoblastoma Susceptibility Gene Encodes a Nuclear Phosphoprotein Associated with DNA Binding Activity" *Nature* 329:642–645 (1987).

Ludlow, J.W., et al., SW40 Large T Antigen Binds Preferentially to an Underphosporylated Member of the Retinoblastoma Susceptibility Gene Product Family: *Cell* 56:57–65 (1989).

Matsuura, Y. et al., "Baculovirus Expression Vectors: the Requirements for High Level Expression of Proteins, Including Glycoproteins" *J. Gen. Virol.* 68:1233–1250 (1987).

Miyamoto, C. et al., "Production of Human c–myc Protein in Insect Cells Infected with a Baculovirus Expression Vector" *Mol. Cell. Biol.* 5:2860–2865 (1985).

Pendergast, A.M. et al., "Baculovirus Expression of Functional P210 BAR–ABL Oncogene Product" *Oncogene* 4:759–766 (1989).

Schneider, C., et al., "A One–Step Purification of Membrane Proteins Using a High Efficiency Immunomatrix" *J. Biol. Chem.* 257:10766–10769 (1982).

Shew, J.–Y. et al., "C–Terminal Truncation of the Retinoblastoma Gene Product Leads to Functional Inactivation" *Proc. Natl. Acad. Sci. USA* 87:6–10 (1990).

Simanis, V., et al., "An Immunoaffinity Purification Procedure for SV40 Large T Antigen" *Virology* 144:88–100 (1985).

Summers, M.D. et al., "A Manual of Methods for Baculovirus Vectors and Insect Cell Culture Procedures" *Texas Agricultural Experiment Station Bulletin No. 1555* (1987).

Wang, N.P., et al., "Expression of the Human Retinoblastoma Gene Product pp110RB in Insect Cells Using the Baculovirus System" *Cell Growth & Differ.* 1:429–437 (1990).

Whyte, P., et al., "Association Between an Oncogene and an Anti–Oncogene: the Adenovirus Ela Proteins Bind to the Retinoblastoma Gene Product" *Nature* 334:124–129 (1988).

Bowen, B. et al., "The Detection of DNA–Binding Proteins by Protein Blotting" *Nucleic Acids Res.* 8:1–21 (1980).

DeCaprio, J.A., et al., "SV40 Large Tumor Antigen Forms a Specific Complex with the Product of the Retinoblastoma Susceptibility Gene" *Cell* 54:275–283 (1988).

Dixon, R.A.F., et al., "Purification of Simian Virus 40 Large T Antigen by Immunoaffinity Chromatography" *J. Virol.* 53:1001–1004 (1985).

Dyson, N., et al., "The Human Papilloma Virus–16 E7 Oncoprotein is Able to Bind to the Retinoblastoma Gene Product" *Science* 243:934–937 (1989).

Giam, Jeang K., et al., "Abundant Synthesis of Functional Human T–Cell Leukemia Virus Type I p40x Protein in Eucaryotic Cells By Using A Baculovirus Vector" *J. Virol.* 16:708–713 (1987).

Gluzman, Y., "SV40–Transformed Simian Cells Support the Replication of Early SV40 Mutants" *Cell* 23:175–182 (1981).

Huang, S., et al., "A Cellular Protein that Competes with SV40 T Antigen for Binding to the Retinoblastoma Gene Product" *Nature* 350:160–162 (1991).

Huang, S. et al., "Two Distinct and Frequently Mutated Regions of Retinoblastoma Protein are Required for Binding to SV40 T Antigen" *EMBO J.* 9:1815–1822 (1990).

Lalande, Marc, et al., "Isolation of Human Chromosome 13—Specific DNA Sequences Cloned from Flow Sorted Chromosomes and Potentially Linked to the Retinoblastoma Locus". *Cancer Genetics and Cytogenetics* 13:283–295 (1984).

Smith, Gale E. et al., Production of Human Beta Interferon in Insect Cells Infected with a Baculovirus Expression Vector. *Mole. and Cell. Biol.* 3:2156–2165 (1983).

Doerfler, W. "Expression of the *Autographa californica* Nuclear Polyhedrosis Virus Genome in Insect Cells: Homologous Viral and Heterologous Vertebrate Genes—The Baculovirus Vector System". *Current Topic in Microbiology and Immunology.* 131:51–68 (1986).

Friend, Stephan H., et al.,"A Human DNA Segment with Properties of the Gene that Predisposes to Retinoblastoma and Osteosarcoma." *Nature.* 323:643–646 (1986).

Fung, Yuen–Kai T. et al., "Structural Evidence for the Authenticity ofthe Human Retinoblastoma Gene". *Science.* 236:1657–1661 (1987).

(List continued on next page.)

*Primary Examiner*—Suzanne E. Ziska
*Attorney, Agent, or Firm*—Townsend and Townsend and Crew LLP

[57] ABSTRACT

A method that produces substantial quantities of a desired polypeptide, by delivering genetic material into insect cells. For example, cloned genes, or gene fragments or, derivates may be defined, utilizing as appropriate vector, into host cells for high level production of high purity protein in substantial quantities.

7 Claims, 5 Drawing Sheets

OTHER PUBLICATIONS

Angier, Natalie "Light Cast on A Darkling Gene". Discover:Mar. 85–96 (1987).

Doerfler, W. Current Topics in Microbiology & Immunology vol. 131; pp. 51–68. 1986. Springer–Verlag. Berlin.

Fung et al Science 236: 1657, 1987.

Smith et al Mol. Cell. Biol 3(12) :2156, 1983.

Lee et al Science 235: 1394, 1987.

Friend et al Nature 323 : 643, 1986.

Angier et al Discover, Mar., 1987 pp. 85–96.

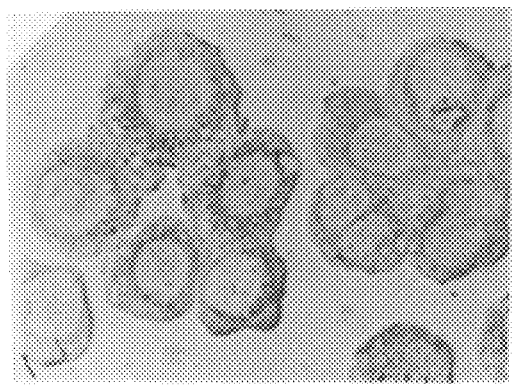 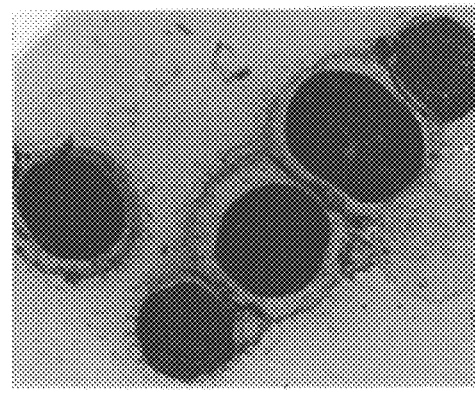
FIG. 3A.    FIG. 3B.
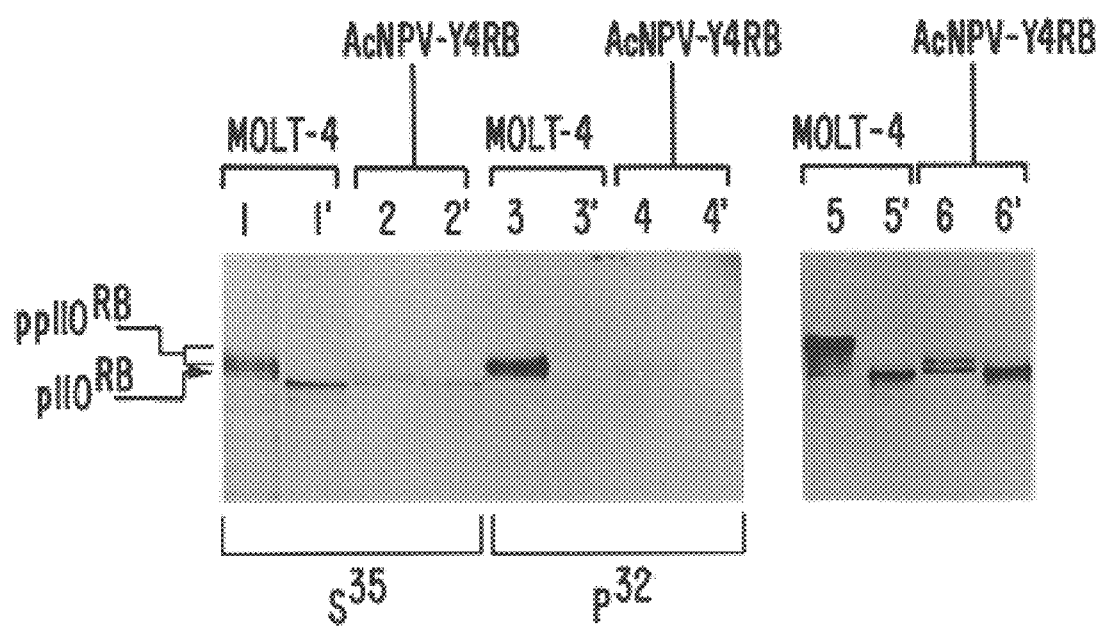
FIG. 4.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 2995 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 139..2922

(xi) SEQUENCE DESCRIPTION: SEQ ID NO:1:

```
TTCCGGTTTT TCTCAGGGGA CGTTGAAATT ATTTTTGTAA CGGGAGTCGG GAGAGGACGG        60

GGCGTGCCCC GCGTGCGCGC GCGTCGTCCT CCCCGGCGCT CCTCCACAGC TCGCTGGCTC       120

CCGCCGCGGA AAGGCGTC ATG CCG CCC AAA ACC CCC CGA AAA ACG GCC GCC        171
                    Met Pro Pro Lys Thr Pro Arg Lys Thr Ala Ala
                     1               5                  10

ACC GCC GCC GCT GCC GCC GCG GAA CCC CCG GCA CCG CCG CCG CCG CCC        219
Thr Ala Ala Ala Ala Ala Ala Glu Pro Pro Ala Pro Pro Pro Pro Pro
                15                  20                  25

CCT CCT GAG GAG GAC CCA GAG CAG GAC AGC GGC CCG GAG GAC CTG CCT        267
Pro Pro Glu Glu Asp Pro Glu Gln Asp Ser Gly Pro Glu Asp Leu Pro
            30                  35                  40

CTC GTC AGG CTT GAG TTT GAA GAA ACA GAA GAA CCT GAT TTT ACT GCA        315
Leu Val Arg Leu Glu Phe Glu Glu Thr Glu Glu Pro Asp Phe Thr Ala
        45                  50                  55

TTA TGT CAG AAA TTA AAG ATA CCA GAT CAT GTC AGA GAG AGA GCT TGG        363
Leu Cys Gln Lys Leu Lys Ile Pro Asp His Val Arg Glu Arg Ala Trp
60                  65                  70                  75

TTA ACT TGG GAG AAA GTT TCA TCT GTG GAT GGA GTA TTG GGA GGT TAT        411
Leu Thr Trp Glu Lys Val Ser Ser Val Asp Gly Val Leu Gly Gly Tyr
                80                  85                  90

ATT CAA AAG AAA AAG GAA CTG TGG GGA ATC TGT ATC TTT ATT GCA GCA        459
Ile Gln Lys Lys Lys Glu Leu Trp Gly Ile Cys Ile Phe Ile Ala Ala
            95                 100                 105

GTT GAC CTA GAT GAG ATG TCG TTC ACT TTT ACT GAG CTA CAG AAA AAC        507
Val Asp Leu Asp Glu Met Ser Phe Thr Phe Thr Glu Leu Gln Lys Asn
        110                 115                 120
```

```
ATA GAA ATC AGT GTC CAT AAA TTC TTT AAC TTA CTA AAA GAA ATT GAT      555
Ile Glu Ile Ser Val His Lys Phe Phe Asn Leu Leu Lys Glu Ile Asp
        125                 130                 135

ACC AGT ACC AAA GTT GAT AAT GCT ATG TCA AGA CTG TTG AAG AAG TAT      603
Thr Ser Thr Lys Val Asp Asn Ala Met Ser Arg Leu Leu Lys Lys Tyr
140                 145                 150                 155

GAT GTA TTG TTT GCA CTC TTC AGC AAA TTG GAA AGG ACA TGT GAA CTT      651
Asp Val Leu Phe Ala Leu Phe Ser Lys Leu Glu Arg Thr Cys Glu Leu
                    160                 165                 170

ATA TAT TTG ACA CAA CCC AGC AGT TCG ATA TCT ACT GAA ATA AAT TCT      699
Ile Tyr Leu Thr Gln Pro Ser Ser Ser Ile Ser Thr Glu Ile Asn Ser
                175                 180                 185

GCA TTG GTG CTA AAA GTT TCT TGG ATC ACA TTT TTA TTA GCT AAA GGG      747
Ala Leu Val Leu Lys Val Ser Trp Ile Thr Phe Leu Leu Ala Lys Gly
            190                 195                 200

GAA GTA TTA CAA ATG GAA GAT GAT CTG GTG ATT TCA TTT CAG TTA ATG      795
Glu Val Leu Gln Met Glu Asp Asp Leu Val Ile Ser Phe Gln Leu Met
        205                 210                 215

CTA TGT GTC CTT GAC TAT TTT ATT AAA CTC TCA CCT CCC ATG TTG CTC      843
Leu Cys Val Leu Asp Tyr Phe Ile Lys Leu Ser Pro Pro Met Leu Leu
220                 225                 230                 235

AAA GAA CCA TAT AAA ACA GCT GTT ATA CCC ATT AAT GGT TCA CCT CGA      891
Lys Glu Pro Tyr Lys Thr Ala Val Ile Pro Ile Asn Gly Ser Pro Arg
                    240                 245                 250

ACA CCC AGG CGA GGT CAG AAC AGG AGT GCA CGG ATA GCA AAA CAA CTA      939
Thr Pro Arg Arg Gly Gln Asn Arg Ser Ala Arg Ile Ala Lys Gln Leu
                255                 260                 265

GAA AAT GAT ACA AGA ATT ATT GAA GTT CTC TGT AAA GAA CAT GAA TGT      987
Glu Asn Asp Thr Arg Ile Ile Glu Val Leu Cys Lys Glu His Glu Cys
            270                 275                 280

AAT ATA GAT GAG GTG AAA AAT GTT TAT TTC AAA AAT TTT ATA CCT TTT     1035
Asn Ile Asp Glu Val Lys Asn Val Tyr Phe Lys Asn Phe Ile Pro Phe
        285                 290                 295

ATG AAT TCT CTT GGA CTT GTA ACA TCT AAT GGA CTT CCA GAG GTT GAA     1083
Met Asn Ser Leu Gly Leu Val Thr Ser Asn Gly Leu Pro Glu Val Glu
300                 305                 310                 315

AAT CTT TCT AAA CGA TAC GAA GAA ATT TAT CTT AAA AAT AAA GAT CTA     1131
Asn Leu Ser Lys Arg Tyr Glu Glu Ile Tyr Leu Lys Asn Lys Asp Leu
                    320                 325                 330

GAT GCA AGA TTA TTT TTG GAT CAT GAT AAA ACT CTT CAG ACT GAT TCT     1179
Asp Ala Arg Leu Phe Leu Asp His Asp Lys Thr Leu Gln Thr Asp Ser
                335                 340                 345

ATA GAC AGT TTT GAA ACA CAG AGA ACA CCA CGA AAA AGT AAC CTT GAT     1227
Ile Asp Ser Phe Glu Thr Gln Arg Thr Pro Arg Lys Ser Asn Leu Asp
            350                 355                 360

GAA GAG GTG AAT GTA ATT CCT CCA CAC ACT CCA GTT AGG ACT GTT ATG     1275
Glu Glu Val Asn Val Ile Pro Pro His Thr Pro Val Arg Thr Val Met
        365                 370                 375

AAC ACT ATC CAA CAA TTA ATG ATG ATT TTA AAT TCA GCA AGT GAT CAA     1323
Asn Thr Ile Gln Gln Leu Met Met Ile Leu Asn Ser Ala Ser Asp Gln
380                 385                 390                 395

CCT TCA GAA AAT CTG ATT TCC TAT TTT AAC AAC TGC ACA GTG AAT CCA     1371
Pro Ser Glu Asn Leu Ile Ser Tyr Phe Asn Asn Cys Thr Val Asn Pro
                    400                 405                 410

AAA GAA AGT ATA CTG AAA AGA GTG AAG GAT ATA GGA TAC ATC TTT AAA     1419
Lys Glu Ser Ile Leu Lys Arg Val Lys Asp Ile Gly Tyr Ile Phe Lys
                415                 420                 425

GAG AAA TTT GCT AAA GCT GTG GGA CAG GGT TGT GTC GAA ATT GGA TCA     1467
Glu Lys Phe Ala Lys Ala Val Gly Gln Gly Cys Val Glu Ile Gly Ser
            430                 435                 440
```

```
CAG CGA TAC AAA CTT GGA GTT CGC TTG TAT TAC CGA GTA ATG GAA TCC       1515
Gln Arg Tyr Lys Leu Gly Val Arg Leu Tyr Tyr Arg Val Met Glu Ser
        445                 450                 455

ATG CTT AAA TCA GAA GAA GAA CGA TTA TCC ATT CAA AAT TTT AGC AAA       1563
Met Leu Lys Ser Glu Glu Glu Arg Leu Ser Ile Gln Asn Phe Ser Lys
460                 465                 470                 475

CTT CTG AAT GAC AAC ATT TTT CAT ATG TCT TTA TTG GCG TGC GCT CTT       1611
Leu Leu Asn Asp Asn Ile Phe His Met Ser Leu Leu Ala Cys Ala Leu
                    480                 485                 490

GAG GTT GTA ATG GCC ACA TAT AGC AGA AGT ACA TCT CAG AAT CTT GAT       1659
Glu Val Val Met Ala Thr Tyr Ser Arg Ser Thr Ser Gln Asn Leu Asp
                495                 500                 505

TCT GGA ACA GAT TTG TCT TTC CCA TGG ATT CTG AAT GTG CTT AAT TTA       1707
Ser Gly Thr Asp Leu Ser Phe Pro Trp Ile Leu Asn Val Leu Asn Leu
            510                 515                 520

AAA GCC TTT GAT TTT TAC AAA GTG ATC GAA AGT TTT ATC AAA GCA GAA       1755
Lys Ala Phe Asp Phe Tyr Lys Val Ile Glu Ser Phe Ile Lys Ala Glu
        525                 530                 535

GGC AAC TTG ACA AGA GAA ATG ATA AAA CAT TTA GAA CGA TGT GAA CAT       1803
Gly Asn Leu Thr Arg Glu Met Ile Lys His Leu Glu Arg Cys Glu His
540                 545                 550                 555

CGA ATC ATG GAA TCC CTT GCA TGG CTC TCA GAT TCA CCT TTA TTT GAT       1851
Arg Ile Met Glu Ser Leu Ala Trp Leu Ser Asp Ser Pro Leu Phe Asp
                    560                 565                 570

CTT ATT AAA CAA TCA AAG GAC CGA GAA GGA CCA ACT GAT CAC CTT GAA       1899
Leu Ile Lys Gln Ser Lys Asp Arg Glu Gly Pro Thr Asp His Leu Glu
                575                 580                 585

TCT GCT TGT CCT CTT AAT CTT CCT CTC CAG AAT AAT CAC ACT GCA GCA       1947
Ser Ala Cys Pro Leu Asn Leu Pro Leu Gln Asn Asn His Thr Ala Ala
            590                 595                 600

GAT ATG TAT CTT TCT CCT GTA AGA TCT CCA AAG AAA AAA GGT TCA ACT       1995
Asp Met Tyr Leu Ser Pro Val Arg Ser Pro Lys Lys Lys Gly Ser Thr
        605                 610                 615

ACG CGT GTA AAT TCT ACT GCA AAT GCA GAG ACA CAA GCA ACC TCA GCC       2043
Thr Arg Val Asn Ser Thr Ala Asn Ala Glu Thr Gln Ala Thr Ser Ala
620                 625                 630                 635

TTC CAG ACC CAG AAG CCA TTG AAA TCT ACC TCT CTT TCA CTG TTT TAT       2091
Phe Gln Thr Gln Lys Pro Leu Lys Ser Thr Ser Leu Ser Leu Phe Tyr
                    640                 645                 650

AAA AAA GTG TAT CGG CTA GCC TAT CTC CGG CTA AAT ACA CTT TGT GAA       2139
Lys Lys Val Tyr Arg Leu Ala Tyr Leu Arg Leu Asn Thr Leu Cys Glu
                655                 660                 665

CGC CTT CTG TCT GAG CAC CCA GAA TTA GAA CAT ATC ATC TGG ACC CTT       2187
Arg Leu Leu Ser Glu His Pro Glu Leu Glu His Ile Ile Trp Thr Leu
            670                 675                 680

TTC CAG CAC ACC CTG CAG AAT GAG TAT GAA CTC ATG AGA GAC AGG CAT       2235
Phe Gln His Thr Leu Gln Asn Glu Tyr Glu Leu Met Arg Asp Arg His
        685                 690                 695

TTG GAC CAA ATT ATG ATG TGT TCC ATG TAT GGC ATA TGC AAA GTG AAG       2283
Leu Asp Gln Ile Met Met Cys Ser Met Tyr Gly Ile Cys Lys Val Lys
700                 705                 710                 715

AAT ATA GAC CTT AAA TTC AAA ATC ATT GTA ACA GCA TAC AAG GAT CTT       2331
Asn Ile Asp Leu Lys Phe Lys Ile Ile Val Thr Ala Tyr Lys Asp Leu
                    720                 725                 730

CCT CAT GCT GTT CAG GAG ACA TTC AAA CGT GTT TTG ATC AAA GAA GAG       2379
Pro His Ala Val Gln Glu Thr Phe Lys Arg Val Leu Ile Lys Glu Glu
                735                 740                 745

GAG TAT GAT TCT ATT ATA GTA TTC TAT AAC TCG GTC TTC ATG CAG AGA       2427
Glu Tyr Asp Ser Ile Ile Val Phe Tyr Asn Ser Val Phe Met Gln Arg
```

-continued

```
         750                 755                  760
CTG AAA ACA AAT ATT TTG CAG TAT GCT TCC ACC AGG CCC CCT ACC TTG          2475
Leu Lys Thr Asn Ile Leu Gln Tyr Ala Ser Thr Arg Pro Pro Thr Leu
    765                 770                  775

TCA CCA ATA CCT CAC ATT CCT CGA AGC CCT TAC AAG TTT CCT AGT TCA          2523
Ser Pro Ile Pro His Ile Pro Arg Ser Pro Tyr Lys Phe Pro Ser Ser
780                 785                  790                  795

CCC TTA CGG ATT CCT GGA GGG AAC ATC TAT ATT TCA CCC CTG AAG AGT          2571
Pro Leu Arg Ile Pro Gly Gly Asn Ile Tyr Ile Ser Pro Leu Lys Ser
                    800                  805                  810

CCA TAT AAA ATT TCA GAA GGT CTG CCA ACA CCA ACA AAA ATG ACT CCA          2619
Pro Tyr Lys Ile Ser Glu Gly Leu Pro Thr Pro Thr Lys Met Thr Pro
            815                  820                  825

AGA TCA AGA ATC TTA GTA TCA ATT GGT GAA TCA TTC GGG ACT TCT GAG          2667
Arg Ser Arg Ile Leu Val Ser Ile Gly Glu Ser Phe Gly Thr Ser Glu
        830                  835                  840

AAG TTC CAG AAA ATA AAT CAG ATG GTA TGT AAC AGC GAC CGT GTG CTC          2715
Lys Phe Gln Lys Ile Asn Gln Met Val Cys Asn Ser Asp Arg Val Leu
    845                  850                  855

AAA AGA AGT GCT GAA GGA AGC AAC CCT CCT AAA CCA CTG AAA AAA CTA          2763
Lys Arg Ser Ala Glu Gly Ser Asn Pro Pro Lys Pro Leu Lys Lys Leu
860                  865                  870                  875

CGC TTT GAT ATT GAA GGA TCA GAT GAA GCA GAT GGA AGT AAA CAT CTC          2811
Arg Phe Asp Ile Glu Gly Ser Asp Glu Ala Asp Gly Ser Lys His Leu
                     880                  885                  890

CCA GGA GAG TCC AAA TTT CAG CAG AAA CTG GCA GAA ATG ACT TCT ACT          2859
Pro Gly Glu Ser Lys Phe Gln Gln Lys Leu Ala Glu Met Thr Ser Thr
             895                  900                  905

CGA ACA CGA ATG CAA AAG CAG AAA ATG AAT GAT AGC ATG GAT ACC TCA          2907
Arg Thr Arg Met Gln Lys Gln Lys Met Asn Asp Ser Met Asp Thr Ser
         910                  915                  920

AAC AAG GAA GAG AAA TGAGGATCTC AGGACCTTGG TGGACACTGT GTACACCTCT          2962
Asn Lys Glu Glu Lys
     925

GGATTCATTG TCTCTCACAG ATGTGACTGA TAT                                     2995
```

(2) INFORMATION FOR SEQ ID NO:2:

(i) SEQUENCE CHARACTERISTICS:
        (A) LENGTH: 928 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Pro Lys Thr Pro Arg Lys Thr Ala Ala Thr Ala Ala Ala Ala
 1               5                  10                  15

Ala Ala Glu Pro Pro Ala Pro Pro Pro Pro Pro Glu Glu Asp
            20                  25                  30

Pro Glu Gln Asp Ser Gly Pro Glu Asp Leu Pro Leu Val Arg Leu Glu
            35                  40                  45

Phe Glu Glu Thr Glu Glu Pro Asp Phe Thr Ala Leu Cys Gln Lys Leu
        50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Ala Val Asp Leu Asp Glu
```

```
                    100                 105                 110
Met Ser Phe Thr Phe Thr Glu Leu Gln Lys Asn Ile Glu Ile Ser Val
            115                 120                 125

His Lys Phe Phe Asn Leu Leu Lys Glu Ile Asp Thr Ser Thr Lys Val
            130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
            195                 200                 205

Glu Asp Asp Leu Val Ile Ser Phe Gln Leu Met Leu Cys Val Leu Asp
            210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
            275                 280                 285

Lys Asn Val Tyr Phe Lys Asn Phe Ile Pro Phe Met Asn Ser Leu Gly
            290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
                340                 345                 350

Thr Gln Arg Thr Pro Arg Lys Ser Asn Leu Asp Glu Glu Val Asn Val
            355                 360                 365

Ile Pro Pro His Thr Pro Val Arg Thr Val Met Asn Thr Ile Gln Gln
            370                 375                 380

Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
                405                 410                 415

Lys Arg Val Lys Asp Ile Gly Tyr Ile Phe Lys Glu Lys Phe Ala Lys
                420                 425                 430

Ala Val Gly Gln Gly Cys Val Glu Ile Gly Ser Gln Arg Tyr Lys Leu
            435                 440                 445

Gly Val Arg Leu Tyr Tyr Arg Val Met Glu Ser Met Leu Lys Ser Glu
            450                 455                 460

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                485                 490                 495

Thr Tyr Ser Arg Ser Thr Ser Gln Asn Leu Asp Ser Gly Thr Asp Leu
                500                 505                 510

Ser Phe Pro Trp Ile Leu Asn Val Leu Asn Leu Lys Ala Phe Asp Phe
            515                 520                 525
```

-continued

```
Tyr Lys Val Ile Glu Ser Phe Ile Lys Ala Gly Asn Leu Thr Arg
    530                 535                 540
Glu Met Ile Lys His Leu Glu Arg Cys Glu His Arg Ile Met Glu Ser
545                 550                 555                 560
Leu Ala Trp Leu Ser Asp Ser Pro Leu Phe Asp Leu Ile Lys Gln Ser
                565                 570                 575
Lys Asp Arg Glu Gly Pro Thr Asp His Leu Glu Ser Ala Cys Pro Leu
                580                 585                 590
Asn Leu Pro Leu Gln Asn Asn His Thr Ala Ala Asp Met Tyr Leu Ser
            595                 600                 605
Pro Val Arg Ser Pro Lys Lys Lys Gly Ser Thr Thr Arg Val Asn Ser
            610                 615                 620
Thr Ala Asn Ala Glu Thr Gln Ala Thr Ser Ala Phe Gln Thr Gln Lys
625                 630                 635                 640
Pro Leu Lys Ser Thr Ser Leu Ser Leu Phe Tyr Lys Lys Val Tyr Arg
                645                 650                 655
Leu Ala Tyr Leu Arg Leu Asn Thr Leu Cys Glu Arg Leu Leu Ser Glu
            660                 665                 670
His Pro Glu Leu Glu His Ile Ile Trp Thr Leu Phe Gln His Thr Leu
            675                 680                 685
Gln Asn Glu Tyr Glu Leu Met Arg Asp Arg His Leu Asp Gln Ile Met
690                 695                 700
Met Cys Ser Met Tyr Gly Ile Cys Lys Val Lys Asn Ile Asp Leu Lys
705                 710                 715                 720
Phe Lys Ile Ile Val Thr Ala Tyr Lys Asp Leu Pro His Ala Val Gln
                725                 730                 735
Glu Thr Phe Lys Arg Val Leu Ile Lys Glu Glu Glu Tyr Asp Ser Ile
            740                 745                 750
Ile Val Phe Tyr Asn Ser Val Phe Met Gln Arg Leu Lys Thr Asn Ile
            755                 760                 765
Leu Gln Tyr Ala Ser Thr Arg Pro Pro Thr Leu Ser Pro Ile Pro His
    770                 775                 780
Ile Pro Arg Ser Pro Tyr Lys Phe Pro Ser Ser Pro Leu Arg Ile Pro
785                 790                 795                 800
Gly Gly Asn Ile Tyr Ile Ser Pro Leu Lys Ser Pro Tyr Lys Ile Ser
                805                 810                 815
Glu Gly Leu Pro Thr Pro Thr Lys Met Thr Pro Arg Ser Arg Ile Leu
            820                 825                 830
Val Ser Ile Gly Glu Ser Phe Gly Thr Ser Glu Lys Phe Gln Lys Ile
            835                 840                 845
Asn Gln Met Val Cys Asn Ser Asp Arg Val Leu Lys Arg Ser Ala Glu
850                 855                 860
Gly Ser Asn Pro Pro Lys Pro Leu Lys Lys Leu Arg Phe Asp Ile Glu
865                 870                 875                 880
Gly Ser Asp Glu Ala Asp Gly Ser Lys His Leu Pro Gly Glu Ser Lys
                885                 890                 895
Phe Gln Gln Lys Leu Ala Glu Met Thr Ser Thr Arg Thr Arg Met Gln
            900                 905                 910
Lys Gln Lys Met Asn Asp Ser Met Asp Thr Ser Asn Lys Glu Glu Lys
    915                 920                 925
```

METHOD FOR PRODUCING RETINOBLASTOMA GENE PROTEIN PRODUCTS

This application is a continuation application of U.S. Ser. No. 07/906,008, filed Jun. 26, 1992, now abandoned, which in turn is a continuation application of U.S. Ser. No. 07/553,905, filed Jul. 16, 1990, now abandoned. This application is also is a continuation-in-part application of U.S. Ser. No. 07/091,547, filed Aug. 31, 1987, now U.S. Pat. No. 5,011,773, issued Apr. 30, 1991; U.S. Ser. No. 07/098,612, filed Sep. 17, 1987, now U.S. Pat. No. 4,942,123, issued Jul. 17, 1990; U.S. Ser. No. 07/108,748, filed Oct. 15, 1987, now abandoned; and U.S. Ser. No. 07/265,829, filed Oct. 31, 1988, also now abandoned. The contents of these applications are hereby incorporated by reference into the present disclosure.

This invention was made with Government support under Grant No. EY05758 from the National Institute of Health. The United States government has certain rights in this invention.

TECHNICAL FIELD

This invention relates, in general, to methods for the production of gene protein products.

BACKGROUND ART

Human and animal tissues have been studied, at great length, and numerous defects have been identified at the cellular level. Many of these defects have a genetic basis and are due, in many cases, to a defective or missing gene. The defect may be the result of a point mutation or other cause, leading to a disruption or abnormal change in the nucleotide sequence within the gene itself. The ultimate result of a malfunctioning gene is, of course, the failure to produce gene protein product or, alternatively, the production of gene protein product which is itself defective.

In the event of the identification of a defective gene, in the human or in an animal, gene therapy may be performed. In this regard, a cloned gene may be delivered to the nucleus of the cell to be treated for the purpose of rectifying the abnormal or defective genetic material. The material utilized in this process is expensive to produce, requiring sophisticated laboratory equipment and the practice of sophisticated molecular genetic techniques. Such techniques are not generally available and since they are, for the most part, confined to a relatively small number of highly sophisticated molecular genetic laboratories.

Because of the cost and general unavailability of gene therapeutic methods, alternative forms of cell therapy are desirable. Analysis of the molecular structure and function of the protein product enables conclusions to be drawn as to the health of the gene producing the product. Frequently, gene protein products can be used for evaluation of interaction among genes for, as an example, the determination of the tumor suppression mechanisms of the body. Regarding tumor suppression mechanisms, reference may be made to the foregoing parent patent applications. In order to facilitate the elucidation of gene function and interaction, it would be highly desirable to have methods for producing gene protein products which were reliable, inexpensive, and which could provide large volumes of the protein in a reliable and predictable manner.

In addition to the value of the gene protein product in the elucidation of genetic function and interaction, the protein itself can be used therapeutically for treatment of defective genetic conditions. In such cases, it would be convenient and effective to introduce into a cell, having defective genetic material, the appropriate gene protein product. Delivery of the protein product would, in some cases, be less expensive and more easily accomplished than the therapeutic administration of the genetic material itself.

For protein therapy, reference may be made to the foregoing mentioned related patent application filed contemporaneously herewith.

As a result of an appreciation of the importance of gene protein products, it would be highly advantageous to have available a technique for preparing and isolating gene protein products in substantially purified form. The availability of intact and biochemically active protein in large quantities, would represent a significant advance for studying the biochemical properties and molecular behavior involved in genetic mechanisms, as well as for therapeutic applications.

In general, for laboratory purposes as distinct from large scale production, gene protein products have been procured from cells, as well as by synthetic production thereof. With regard to derivation from cells, cellular proteins exist only in very small quantities. As a result, it is not practical to attempt to derive sufficiently large quantities of the protein from natural sources.

With regard to synthetic methods of production, attempts to express protein by introducing the coding sequence of a gene into a bacterial expression vector, have only been partially successful. Bacterially produced proteins have poor solubility. Another drawback of using a bacterial expression system is that bacterial cells are unable to modify eukaryotic proteins, and analysis of such proteins could be misleading, if post-translational modifications are required for the normal function of the protein. In summary, bacterially produced proteins generally have poor solubility and may be molecularly defective, thereby limiting their value.

Conventional laboratory techniques for making protein products have suffered from an inability to produce sufficiently large quantities, but also the resulting products have not been sufficiently pure, on a consistent basis. As a representative example of the difficulty in the production of some protein products, TrpE-RB fusion proteins have been developed and a T7 RNA polymerase expression has been utilized, expressing in $E.\,coli$, for production of the polypeptide. These methods have proven to be relatively complicated, requiring the practice of sophisticated biochemical techniques. In addition, such methods have serious limitations, since they are capable of producing only very small amounts of the desired polypeptide. In addition, the polypeptides produced by such methods are often not molecularly suitable, as for example, not being phosphorylated.

Therefore, in view of the importance of the gene product polypeptides, it would be highly desirable to have a method for producing such polypeptides, in substantial quantities, having desired biochemical and biophysical characteristics.

DISCLOSURE OF INVENTION

It is a primary object of this invention to provide methods for producing substantial amounts of intact and active gene product polypeptides.

It is a further object of this invention to provide methods for the production of specific gene product polypeptides which are identical in structure and function to naturally occurring polypeptides.

Briefly, the above and further objects of the present invention are realized by providing a method for producing substantial quantities of a desired polypeptide, by delivering genetic material into insect cells. For example, cloned genes, or gene fragments or, derivatives may be delivered, utilizing an appropriate vector, into host cells for high level production of high purity protein in substantial quantities.

A significant advantage of the present invention is that it provides a technique for producing substantial quantities of high quality polypeptides for investigation of gene function, at the cellular level.

Another advantage of the present invention is that it provides a technique for such production in a convenient, reliable and repetitive manner, at relatively low cost.

A further advantage of the present invention is that it provides substantial quantities of high quality polypeptides for elucidation of interactions among genes at the cellular and subcellular levels.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein:

FIG. 3A is a photomicrograph depicting intracellular localization of RB protein;

FIG. 3B is a photomicrograph of infected Sf9 cells;

FIG. 4 is an autoradiograph depicting phosphorylation of RB protein in insect cells and the results of dephosphorylation analysis;

BEST MODE FOR CARRYING OUT THE INVENTION

Figure 1:
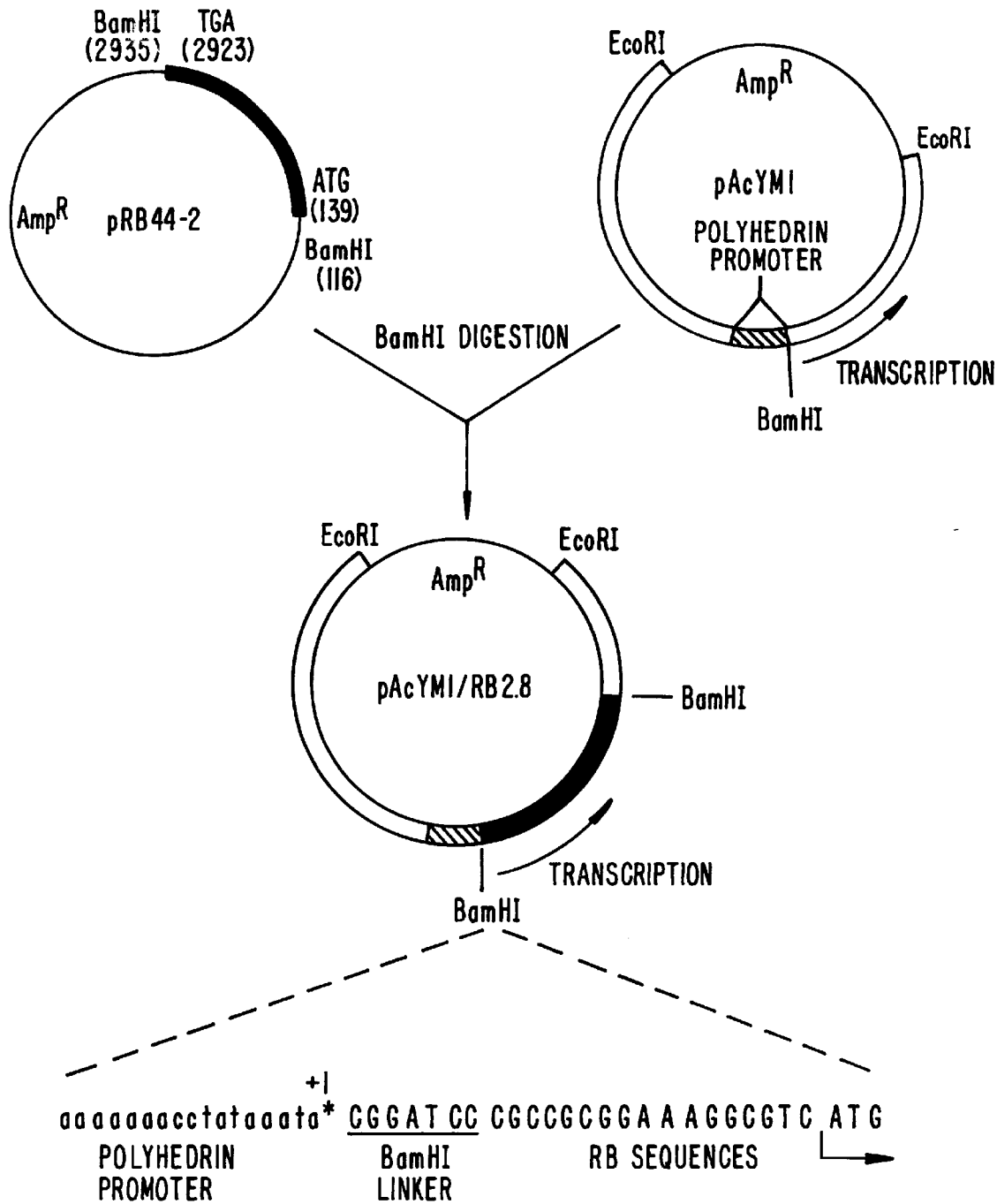
FIG. 1 is a diagrammatic representation of the construction of the baculovirus expression vector for $pp110^{RB}$ synthesis.

All references cited in this Application are hereby incorporated by reference and made part of this application. The detailed description is arranged according to the following outline:

A. GENERAL DESCRIPTION.
B. RB GENE PRODUCT EXAMPLE.
  B2. THE CONSTRUCTION OF RECOMBINANT BACULOVIRUS.
  B2. EXPRESSION OF EXOGENOUS RB PROTEIN IN INFECTED INSECT CELLS.
  B3. NUCLEAR LOCALIZATION AND POST-TRANSLATIONAL PHOSPHORYLATION OF EXOGENOUS RB PROTEIN.
  B4. PURIFICATION OF RB PROTEIN FROM INFECTED INSECT CELLS.
  B5. DNA-BINDING ACTIVITY AND SPECIFIC COMPLEX FORMATION WITH SV40 T ANTIGEN.
  B6. NUCLEAR TRANSLOCATION OF PURIFIED RB PROTEIN.
  B7. SUMMARY

A. General Description

A method has been invented for the production of gene protein, by the delivery of genetic material to insect cell cultures for production, by the culture, of a specific gene protein product. Utilizing the present invention, high titers of substantially purified, intact and biochemically active proteins have been produced.

The expression system of the present invention has broad applications. Thus, for example, cloned human and animal genes, and fragments, homologs, derivatives and portions thereof, may be utilized for the production of the desired protein product. The protein product thus produced, of course, has utility in treatment of defective cells and in the elucidation of gene functions, as the genes interact with one another at the cellular level.

In producing the gene protein product, it has been found that insect cell cultures, since they are eukaryotic in character, are suitable. Conventional vectors, such as viral vectors, may be used for delivery of the genetic material to the cell culture.

For example, viral vectors of insect cell culture have been utilized for the production of the RB gene protein product. In this regard, the baculovirus, *Autographa californica* nuclear polyhedrosis virus (AcNPV), is utilized as a helper-independent viral expression vector for the high-level production of recombinant proteins in cultured insect cells. The virus is propagated in cultured Fall Army worm *Spodoptera frugiperda* (Sf9) cells. The virus has a strong temporally regulated promotor of the polyhedrin gene, whose product represents 50% or more of total cellular proteins during a lytic infection. By in vivo recombination, the coding sequence of a foreign gene is placed under the transcriptional control of the polyhedrin promoter, resulting in a high level of protein expression. In addition, the proteins so produced are correctly folded and contain appropriate post-translational modifications similar to those proteins in the original higher eukaryotes.

B. RB Gene Product Example

The following is a more detailed description of the inventive method for the production of the $pp110^{RB}$ protein. For additional information relating to such protein, as well as the retinoblastoma gene, reference may be made to the above mentioned parent patent applications.

Elucidation of the biochemical properties and biological functions of cancer suppressor gene products, such as the RB gene, has been hampered by difficulty in obtaining sufficient quantities of purified protein. This is due, in part, because of its low abundance in cells and, in addition, because attempts to express protein by introducing the coding sequence of the gene into a bacterial expression vector have only been partially successful. Based on these considerations, it was concluded that the problems presented by current technique could be circumvented by expressing a cloned gene in an eukaryotic system. While the specific example of the present invention relates to production of the RB gene protein product, the present invention has utility for, and is related to, the production of the protein products of other eukaryotic genes, including, but not limited to, the cancer suppressor genes.

The baculovirus *Autographa californica* nuclear polyhedrosis virus (AcNPV) is known to be suitable as a helper-independent viral expression vector for the high-level production of recombinant proteins in cultured insect cells. This virus propagates in cultured Fall Army worm *Spodoptera frugiperda* (Sf9) cells and has a strong temporally regulated promotor of the polyhedrin gene, whose product represents 50% or more of total cellular proteins during a lytic infection. By in vivo recombination, the coding sequence of a foreign gene can be placed under the transcriptional control of the polyhedrin promoter, resulting in a high level of protein expression. In addition, such proteins may be correctly folded and contain appropriate post-translational modifications like those proteins in the original higher eukaryotes.

To test the feasibility of expressing functional RB protein by the baculovirus system, cloned human RB cDNA, containing the complete coding sequence of the RB gene, was introduced into the ACNPV expression vector and the recombinant viruses were propagated in insect cells.

```
          TTCCGGTTTT TCTCAGGGGA CGTTGAAATT ATTTTTGTAA CGGGAGTCGG GAGAGGACGG    60
          GGCGTGCCCC GCGTGCGCGC GCGTCGTCCT CCCCGGCGCT CCTCCACAGC TCGCTGGCTC   120
          CCGCCGCGGA AAGGCGTC ATG CCG CCC AAA ACC CCC CGA AAA ACG GCC GCC      171
                            Met Pro Pro Lys Thr Pro Arg Lys Thr Ala Ala
                             1               5                      10

ACC GCC GCC GCT GCC GCC GCG GAA CCC CCG GCA CCG CCG CCG CCG CCC              219
Thr Ala Ala Ala Ala Ala Ala Glu Pro Pro Ala Pro Pro Pro Pro Pro
                15                  20                  25

CCT CCT GAG GAG GAC CCA GAG CAG GAC AGC GGC CCG GAG GAC CTG CCT              267
Pro Pro Glu Glu Asp Pro Glu Gln Asp Ser Gly Pro Glu Asp Leu Pro
            30                  35                  40

CTC GTC AGG CTT GAG TTT GAA GAA ACA GAA GAA CCT GAT TTT ACT GCA              315
Leu Val Arg Leu Glu Phe Glu Glu Thr Glu Glu Pro Asp Phe Thr Ala
        45                  50                  55

TTA TGT CAG AAA TTA AAG ATA CCA GAT CAT GTC AGA GAG AGA GCT TGG              363
Leu Cys Gln Lys Leu Lys Ile Pro Asp His Val Arg Glu Arg Ala Trp
 60                  65                  70                  75

TTA ACT TGG GAG AAA GTT TCA TCT GTG GAT GGA GTA TTG GGA GGT TAT              411
Leu Thr Trp Glu Lys Val Ser Ser Val Asp Gly Val Leu Gly Gly Tyr
                80                  85                  90

ATT CAA AAG AAA AAG GAA CTG TGG GGA ATC TGT ATC TTT ATT GCA GCA              459
Ile Gln Lys Lys Lys Glu Leu Trp Gly Ile Cys Ile Phe Ile Ala Ala
                95                  100                 105

GTT GAC CTA GAT GAG ATG TCG TTC ACT TTT ACT GAG CTA CAG AAA AAC              507
Val Asp Leu Asp Glu HeT Ser Phe Thr Phe Thr Glu Leu Gln Lys Asn
            110                 115                 120

ATA GAA ATC AGT GTC CAT AAA TTC TTT AAC TTA CTA AAA GAA ATT GAT              555
Ile Glu Ile Ser Val His Lys Phe Phe Asn Leu Leu Lys Glu Ile Asp
    125                 130                 135

ACC AGT ACC AAA GTT GAT AAT GCT ATG TCA AGA CTG TTG AAG AAG TAT              603
Thr Ser Thr Lys Val Asp Asn Ala Met Ser Arg Leu Leu Lys Lys Tyr
140                 145                 150                 155

GAT GTA TTG TTT GCA CTC TTC AGC AAA TTG GAA AGG ACA TGT GAA CTT              651
Asp Val Leu Phe Ala Leu Phe Ser Lys Leu Glu Arg Thr Cys Glu Leu
                160                 165                 170

ATA TAT TTG ACA CAA CCC AGC AGT TCG ATA TCT ACT GAA ATA AAT TCT              699
Ile Tyr Leu Thr Gln Pro Ser Ser Ser Ile Ser Thr Glu Ile Asn Ser
            175                 180                 185

GCA TTG GTG CTA AAA GTT TCT TGG ATC ACA TTT TTA TTA GCT AAA GGG              747
Ala Leu Val Leu Lys Val Ser Trp Ile Thr Phe Leu Leu Ala Lys Gly
        190                 195                 200

GAA GTA TTA CAA ATG GAA GAT GAT CTG GTG ATT TCA TTT CAG TTA ATG              795
Glu Val Leu Gln Met Glu Asp Asp Leu Val Ile Ser Phe Gln Leu Met
    205                 210                 215

CTA TGT GTC CTT GAC TAT TTT ATT AAA CTC TCA CCT CCC ATG TTG CTC              843
Leu Cys Val Leu Asp Tyr Phe Ile Lys Leu Ser Pro Pro Met Leu Leu
220                 225                 230                 235
```

```
                              -continued
AAA GAA CCA TAT AAA ACA GCT GTT ATA CCC ATT AAT GGT TCA CCT CGA    891
Lys Glu Pro Tyr Lys Thr Ala Val Ile Pro Ile Asn Gly Ser Pro Arg
            240                 245                 250

ACA CCC AGG CGA GGT CAG AAC AGG AGT GCA CGG ATA GCA AAA CAA CTA    939
Thr Pro Arg Arg Gly Gln Asn Arg Ser Ala Arg Ile Ala Lys Gln Leu
            255                 260                 265

GAA AAT GAT ACA AGA ATT ATT GAA GTT CTC TGT AAA GAA CAT GAA TGT    987
Glu Asn Asp Thr Arg Ile Ile Glu Val Leu Cys Lys Glu His Glu Cys
            270                 275                 280

AAT ATA GAT GAG GTG AAA AAT GTT TAT TTC AAA AAT TTT ATA CCT TTT   1035
Asn Ile Asp Glu Val Lys Asn Val Tyr Phe Lys Asn Phe Ile Pro Phe
            285                 290                 295

ATG AAT TCT CTT GGA CTT GTA ACA TCT AAT GGA CTT CCA GAG GTT GAA   1083
Met Asn Ser Leu Gly Leu Val Thr Ser Asn Gly Leu Pro Glu Val Glu
300                 305                 310                 315

AAT CTT TCT AAA CGA TAC GAA GAA ATT TAT CTT AAA AAT AAA GAT CTA   1131
Asn Leu Ser Lys Arg Tyr Glu Glu Ile Tyr Leu Lys Asn Lys Asp Leu
            320                 325                 330

GAT GCA AGA TTA TTT TTG GAT CAT GAT AAA ACT CTT CAG ACT GAT TCT   1179
Asp Ala Arg Leu Phe Leu Asp His Asp Lys Thr Leu Gln Thr Asp Ser
            335                 340                 345

ATA GAC AGT TTT GAA ACA CAG AGA ACA CCA CGA AAA AGTAAC CTT GAT    1227
Ile Asp Ser Phe Glu Thr Gln Arg Thr Pro Arg Lys Ser Asn Leu Asp
            350                 355                 360

GAA GAG GTG AAT GTA ATT CCT CCA CAC ACT CCA GTT AGG ACT GTT ATG   1275
Glu Glu Val Asn Val Ile Pro Pro His Thr Pro Val Arg Thr Val Met
365                 370                 375

AAC ACT ATC CAA CAA TTA ATG ATG ATT TTA AAT TCA GCA AGT GAT CAA   1323
Asn Thr Ile Gln Gln Leu Met Met Ile Leu Asn Ser Ala Ser Asp Gln
380                 385                 390                 395

CCT TCA GAA AAT CTG ATT TCC TAT TTT AAC AAC TGC ACA GTG AAT CCA   1371
Pro Ser Glu Asn Leu Ile Ser Tyr Phe Asn Asn Cys Thr Val Asn Pro
            400                 405                 410

AAA GAA AGT ATA CTG AAA AGA GTG AAG GAT ATA GGA TAC ATC TTT AAA   1419
Lys Glu Ser Ile Leu Lys Arg Val Lys Asp Ile Gly Tyr Ile Phe Lys
            415                 420                 425

GAG AAA TTT GCT AAA GCT GTG GGA CAG GGT TGT GTC GAA ATT GGA TCA   1467
Glu Lys Phe Ala Lys Ala Val Gly Gln Gly Cys Val Glu Ile Gly Ser
            430                 435                 440

CAG CGA TAC AAA CTT GGA GTT CGC TTG TAT TAC CGA GTA ATG GAA TCC   1515
Gln Arg Tyr Lys Leu Gly Val Arg Leu Tyr Tyr Arg Val Met Glu Ser
            445                 450                 455

ATG CTT AAA TCA GAA GAA GAA CGA TTA TCC ATT CAA AAT TTT AGC AAA   1563
Met Leu Lys Ser Glu Glu Glu Arg Leu Ser Ile Gln Asn Phe Ser Lys
460                 465                 470                 475

CTT CTG AAT GAC AAC ATT TTT CAT ATG TCT TTA TTG GCG TGC GCT CTT   1611
Leu Leu Asn Asp Asn Ile Phe His Met Ser Leu Leu Ala Cys Ala Leu
            480                 485                 490

GAG GTT GTA ATG GCC ACA TAT AGC AGA AGT ACA TCT CAG AAT CTT GAT   1659
Glu Val Val Met Ala Thr Tyr Ser Arg Ser Thr Ser Gln Asn Leu Asp
            495                 500                 505

TCT GGA ACA GAT TTG TCT TTC CCA TGG ATT CTG AAT GTG CTT AAT TTA   1707
Ser Gly Thr Asp Leu Ser Phe Pro Trp Ile Leu Asn Val Leu Asn Leu
            510                 515                 520

AAA GCC TTT GAT TTT TAC AAA GTG ATC GAA AGT TTT ATC AAA GCA GAA   1755
Lys Ala Phe Asp Phe Tyr Lys Val Ile Glu Ser Phe Ile Lys Ala Glu
            525                 530                 535

GGC AAC TTG ACA AGA GAA ATG ATA AAA CAT TTA GAA CGA TGT GAA CAT   1803
Gly Asn Leu Thr Arg Glu Met Ile Lys His Leu Glu Arg Cys Glu His
540                 545                 550                 555
```

-continued

| | |
|---|---|
| CGA ATC ATG GAA TCC CTT GCA TGG CTC TCA GAT TCA CCT TTA TTT GAT<br>Arg Ile Met Glu Ser Leu Ala Trp Leu Ser Asp Ser Pro Leu Phe Asp<br>560                         565                            570 | 1851 |
| CTT ATT AAA CAA TCA AAG GAC CGA GAA GGA CCA ACT GAT CAC CTT GAA<br>Ile Lys Gln Ser Lys Asp Arg Glu Gly Pro Thr Asp His Leu Glu<br>575                         580                         585 | 1899 |
| TCT GCT TGT CCT CTT AAT CTT CCT CTC CAG AAT AAT CAC ACT GCA GCA<br>Ser Ala Cys Pro Leu Asn Leu Pro Leu Gln Asn Asn His Thr Ala Ala<br>590                         595                         600 | 1947 |
| GAT ATG TAT CTT TCT CCT GTA AGA TCT CCA AAG AAA AAA GGT TCA ACT<br>Asp Met Tyr Leu Ser Pro Val Arg Ser Pro Lys Lys Lys Gly Ser Thr<br>605                         610                         615 | 1995 |
| ACG CGT GTA AAT TCT ACT GCA AAT GCA GAG ACA CAA GCA ACC TCA GCC<br>Thr Arg Val Asn Ser Thr Ala Asn Ala Glu Thr Gln Ala Thr Ser Ala<br>620                       625                         630                       635 | 2043 |
| TTC CAG ACC CAG AAG CCA TTG AAA TCT ACC TCT CTT TCA CTG TTT TAT<br>Phe Gln Thr Gln Lys Pro Leu Lys Ser Thr Ser Leu Ser Leu Phe Tyr<br>640                         645                         650 | 2091 |
| AAA AAA GTG TAT CGG CTA GCC TAT CTC CGG CTA AAT ACA CTT TGT GAA<br>Lys Lys Val Tyr Arg Leu Ala Tyr Leu Arg Leu Asn Thr Leu Cys Glu<br>655                         660                         665 | 2139 |
| CGC CTT CTG TCT GAG CAC CCA GAA TTA GAA CAT ATC ATC TGG ACC CTT<br>Arg Leu Leu Ser Glu His Pro Glu Leu Glu His Ile Ile Trp Thr Leu<br>670                         675                         680 | 2187 |
| TTC CAG CAC ACC CTG CAG AAT GAG TAT GAA CTC ATG AGA GAC AGG CAT<br>Phe Gln His Thr Leu Gln Asn Glu Tyr Glu Leu Met Arg Asp Arg His<br>685                         690                         695 | 2235 |
| TTG GAC CAA ATT ATG ATG TGT TCC ATG TAT GGC ATA TGC AAA GTG AAG<br>Leu Asp Gln Ile Met Met Cys Ser Met Tyr Gly Ile Cys Lys Val Lys<br>700                       705                         710                       715 | 2283 |
| AAT ATA GAC CTT AAA TTC AAA ATC ATT GTA ACA GCA TAC AAG GAT CTT<br>Asn Ile Asp Leu Lys Phe Lys Ile Ile Val Thr Ala Tyr Lys Asp Leu<br>720                         725                         730 | 2331 |
| CCT CAT GCT GTT CAG GAG ACA TTC AAA CGT GTT TTG ATC AAA GAA GAG<br>Pro His Ala Val Gln Glu Thr Phe Lys Arg Val Leu Ile Lys Glu Glu<br>735                         740                         745 | 2379 |
| GAG TAT GAT TCT ATT ATA GTA TTC TAT AAC TCG GTC TTC ATG CAG AGA<br>Glu Tyr Asp Ser Ile Ile Val Phe Tyr Asn Ser Val Phe Met Gln Arg<br>750                         755                         760 | 2427 |
| CTG AAA ACA AAT ATT TTG CAG TAT GCT TCC ACC AGG CCC CCT ACC TTG<br>Leu Lys Thr Asn Ile Leu Gln Tyr Ala Ser Thr Arg Pro Pro Thr Leu<br>765                         770                         775 | 2475 |
| TCA CCA ATA CCT CAC ATT CCT CGA AGC CCT TAC AAG TTT CCT AGT TCA<br>Ser Pro Ile Pro His Ile Pro Arg Ser Pro Tyr Lys Phe Pro Ser Ser<br>780                         785                         790                       795 | 2523 |
| CCC TTA CGG ATT CCT GGA GGG AAC ATC TAT ATT TCA CCC CTG AAG AGT<br>Pro Leu Arg Ile Pro Gly Gly Asn Ile Tyr Ile Ser Pro Leu Lys Ser<br>800                         805                         810 | 2571 |
| CCA TAT AAA ATT TCA GAA GGT CTG CCA ACA CCA ACA AAA ATG ACT CCA<br>Pro Tyr Lys Ile Ser Glu Gly Leu Pro Thr Pro Thr Lys Met Thr Pro<br>815                         820                         825 | 2619 |
| AGA TCA AGA ATC TTA GTA TCA ATT GGT GAA TCA TTC GGG ACT TCT GAG<br>Arg Ser Arg Ile Leu Val Ser Ile Gly Glu Ser Phe Gly Thr Ser Glu<br>830                         835                         840 | 2667 |
| AAG TTC CAG AAA ATA AAT CAG ATG GTA TGT AAC AGC GAC CGT GTG CTC<br>Lys Phe Gln Lys Ile Asn Gln Met Val Cys Asn Ser Asp Arg Val Leu<br>845                         850                         855 | 2715 |
| AAA AGA AGT GCT GAA GGA AGC AAC CCT CCT AAA CCA CTG AAA AAA CTA<br>Lys Arg Ser Ala Glu Gly Ser Asn Pro Pro Lys Pro Leu Lys Lys Leu<br>860                         865                         870                       875 | 2763 |

```
                           -continued
CGC TTT GAT ATT GAA GGA TCA GAT GAA GCA GAT GGA AGT AAA CAT CTC      2811
Arg Phe Asp Ile Glu Gly Ser Asp Glu Ala Asp Gly Ser Lys His Leu
                880                 885                 890

CCA GGA GAG TCC AAA TTT CAG CAG AAA CTG GCA GAA ATG ACT TCT ACT      2859
Pro Gly Glu Ser Lys Phe Gln Gln Lys Leu Ala Glu Met Thr Ser Thr
            895                 900                 905

CGA ACA CGA ATG CAA AAG CAG AAA ATG AAT GAT AGC ATG GAT ACC TCA      2907
Arg Thr Arg Met Gln Lys Gln Lys Met Asn Asp Ser Met Asp Thr Ser
        910                 915                 920

AAC AAG GAA GAG AAA TGAGGATCTC AGGACCTTGG TGGACACTGT GTACACCTCT      2962
Asn Lys Glu Glu Lys
    925

GGATTCATTG TCTCTCACAG ATGTGACTGA TAT                                 2995
```

Successful expression of human pp110$^{RB}$, at high level, by the host-vector system was achieved. The protein produced is phosphorylated and correctly targeted to the nuclei of infected cells. In addition, methods for the purification of RB protein were developed. It was found that the purified protein can bind DNA and form a specific complex with SV40 T antigen in the same way as the authentic human pp110$^{RB}$. The prompt nuclear translocation of the protein after microinjection further suggests the active nature of the purified RB protein.

B1. The Construction of Recombinant Baculovirus

In order to achieve maximal production of the RB protein in the baculovirus expression system, recombinant transfer vectors were constructed with deletion of most of the 5' non-coding sequence of the RB gene. By site-specific mutagenesis, two BamH1 sites were introduced into the RB cDNA at nucleotides 116 and 2935 to facilitate construction of the recombinant transfer vector. As shown in FIG. 1, the resulting pAcYM1/RB2.8 encodes mRNA that contains the entire (60 base pairs) polyhedrin 5' non-coding sequence fused to 23 base pairs of the 5' untranslated region of the RB cDNA, followed by the complete coding sequence. This recombinant gene contains no ATG codons upstream of the authentic RB initiation site at nucleotide 139. Thus, the recombinant gene encodes a non-fusion, full-length RB protein.

Referring now to FIG. 1, there is depicted the transfer vector pAcYM1, which has all the upstream sequences of the polyhedrin gene, including the A of the initiating ATG codon, followed by a unique BamH1 site. The transfer vector has been described by Matsuura et al. *J. Gen. Virol.*, 68: 1233–1250, (1987). pRB44-2 contains the complete RB cDNA coding sequence from nucleotides 116 to 2935 subcloned into the BamH1 site of plasmic pGEM1 (Promega). The recombinant baculovirus vector, pAcYM1/RB2.8, was constructed by inserting the 2.8 kb BamH1 fragment from pRB44-2 into the BamH1 site of pAcYM1 in a proper orientation so that the transcription of the RB gene would be under the direct control of the polyhedrin promoter.

In the construction of the baculovirus expression vector for pp110$^{RB}$ synthesis, the following matters were considered. p$^{RB}$44-2 consists of the complete RB cDNA coding sequence from nucleotide 116 to 2935 subcloned into the BamH1 site of pGEM1. pAcYM1 contains the approximately 7 kb EcoR1 fragment of the viral DNA sequence flanking the polyhedrin gene in which the leader sequence remains intact, but all of the polyhedrin coding sequences except the first A of the ATG are replaced by a BamH1 linker. The recombinant baculovirus vector, pAcYM1/RB2.8, containing polyhedrin promoter-RB cDNA fusion, was constructed by inserting the RB 2.8 kb BamH1 fragment into the BamH1 site of pAcYM1 so that the transcription of the RB gene would be under the direct control of the polyhedrin promoter. The sequence at the junction of the fusion is shown at the bottom of FIG. 1 with the lower case symbol representing the polyhedrin promoter, and the upper case representing the RB cDNA sequence, while the BamH1 linker is underlined. The translation of the fusion gene utilizing the ATG of the RB (nucleotide 139) is indicated by the arrow, whereas a* (+1) of FIG. 1 represents the first A of the translation start codon ATG of the polyhedrin gene.

Transfer of RB cDNA from the recombinant plasmid to the viral genome was achieved by contransfecting pAcYM1/RB2.8 DNA with wild-type *Autographa californica* nuclear polyhedrosis virus DNA by lipofection (BRL). The recombinant viruses, in which the polyhedrin gene had been inactivated by allelic replacement with the RB gene through homologous recombination, were identified by their distinct plaque morphology as they showed no polyhedrin occlusion bodies in infected cells. The viruses were subjected to three rounds of plaque purification to obtain a pure stock of RB-containing baculovirus, which was designated as AcNPV-Y4 RB.

B2. Expression of Exogenus RB Protein in Infected Insect Cells.

Prior to determining whether the AcNPV polyhedrin promotor could drive the expression of human RB gene in heterologous invertebrate cells, Sf9 cells were prepared. Sf9, a clonal isolate of *Spodoptera frugiperda* IPLB-Sf21-AE In vitro, 13: 213–217, (1977) was grown as monolayer or suspension cultures at 27° C. in Grace's insect medium supplemented with 3.33 gm/l of yeastolate, lactalbumin hydrolysate (GIBCO), and 10% heat-inactivated fetal bovine serum (GIMINI) *Bull.* 1555, (1987) (Texas Agricultural Experiment Station, College Station, Tex.). In large-scale preparation of cellular lysates, spinner cultures of Sf9 cells were grown in EX-CELL 400 serum-free defined medium (J.R. Scientific). Molt-4 cells, a human T cell leukemia line, were cultured in suspension in RPMI 1640 supplemented with 20% calf serum. Saos-2 cells, an osteosarcoma cell line, were grown in Dulbecco's modified Eagle's medium supplemented with 7.5% fetal bovine serum.

In determining whether the AcNPV polyhedrin promoter could drive the expression of human RB gene in heterologous invertebrate cells, Sf9 cells were infected with plaque-purified AcNPV-Y4 RB. Forty hours after infection, lysates of the infected cells were collected and immunoprecipitated with anti-RBO.47 antibody. Samples were then subjected to SDS-PAGE, followed by Western blot analysis.

Figure 2A:
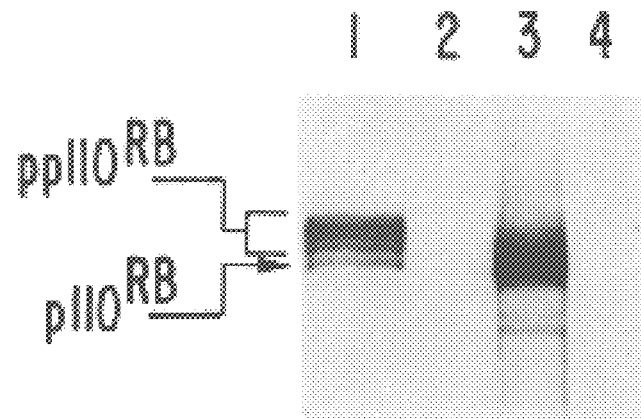
FIG. 2A is a Western blot of ppRB infected insect cells.
Figure 2B:
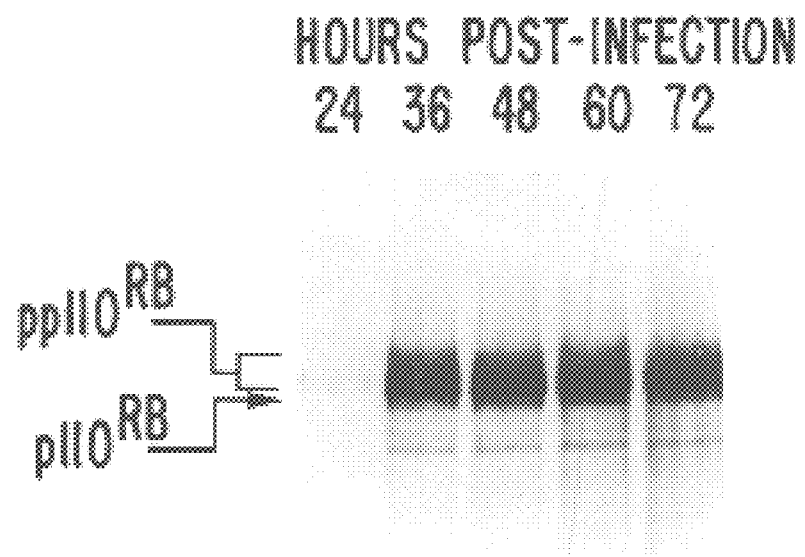
FIG. 2B is a Western blot identifying cellular extracts from infected cells at up to 72 hours post-infection.

Referring now to FIGS. 2A and 2B, there are depicted the identification of pp110$^{RB}$ in AcNPV-Y4 RB infected insect cells, by Western blot analysis. With regard to FIG. 2A, cellular extracts were prepared 40 hours post-infection from mock-infected (lane 2), AcNPV-Y4 RB-infected (lane 3), or wild-type AcNPV-infected Sf9 cells (lane 4). Molt-4, a human leukemia cell line, was used as the control (lane 1).

As shown in FIG. 2A, immunoblotting with pMG3-245 monoclonal antibody revealed the appearance of full-length RB protein similar to that of the mammalian cells (lane 1) in extracts of cells infected with AcNPV-Y4 RB (lane 3), but not in the mock or wild-type AcNPV infected cells (lanes 2 and 4). With regard to FIG. 2B, cellular extracts from AcNPV-Y4 RB infected cells were prepared at different times post-infection, in order to determine the optimal timing for RB protein production. The lysates were immunoprecipitated with anti-RBO.47 antibody and immunoblotted with pMG3-245 monoclonal antibody. In FIG. 2B, p110$^{RB}$ and pp110$^{RB}$ represent unphosphorylated and phosphorylated RB proteins, respectively. The production of the RB protein was monitored during the post-infection period to determine the optimal timing for harvesting the cells. As shown in FIG. 2B, RB protein production can be detected at 24 hours after infection and it is significantly increased during the following 12 hours. The level of protein production was maintained through about 72 hours of infection, at which time significant viral lysis of the cells began. To minimize protein degradation associated with cell lysis, infected cells were routinely harvested around 40 hours post-infection.

In detecting the expression of the RB protein, AcNPV-Y4 RB was used to infect Sf9 cells at a MOI of 0.5. At 24, 36, 48, 60 and 72 hours post-infection, $5 \times 10^4$ cells were lysed in 1 ml lysis buffer (50 mM Tris-HCl, pH 7.4; 0.2% Nonidet P-40; 1 mM EDTA; 100 mM NaCl; 50 mM NaF and 1 mM PMSF), and the lysates were clarified by centrifugation (4° C., 20,000×g) for 5 minutes. Lysates were then incubated with anti-RB0.47 antibody, and immunoprecipitates were separated by 7.5% SDS-PAGE. Proteins were then transferred to nitrocellulose paper, following conventional techniques. After overnight blocking, the nitrocellulose paper was incubated with pMG3-245 anti-fRB monoclonal antibody for 3 hours, followed by alkaline phosphatase-conjugated goat anti-mouse IgG and colorigenic substrates, as described in Cell, 54: 275–283, (1988).

B3. Nuclear Localization and Post-translational Phosphorylation of Exogenus RB Protein The RB gene encodes a nuclear phosphoprotein of Mr 110,000. To determine whether RB protein produced in insect cells with the baculovirus was targeted to the nucleus, AcNPV-Y4 RB-infected Sf9 cells were immunostained with anti-RB0.47 antibody 40 hours after infection. The intracellular localization of RB protein expressed in insect cells by immunostaining is depicted in FIGS. 3A and 3B. FIG. 3A depicts mock-infected Sf9 cells and FIG. 3B depicts AcNPV-Y4 RB-infected Sf9 cells. As shown in FIGS. 3A and 3B, the infected cells contained unusually large nuclei. Such a condition is characteristic of the cytopathic effect of baculovirus infection. When mock-infected or wild-type AcNPV-infected Sf9 cells were incubated with anti-RB0.47 antibody, no staining was observed (FIG. 3A). However, intense staining was found exclusively in the nuclei of cells infected with AcNPV-Y4 RB (FIG. 3B). Analysis by SDS-PAGE and Western blotting of nuclear and cytoplasmic extracts from AcNPV-Y4 RB infected Sf9 cells confirmed that the exogenous RB protein is present predominantly in the nuclear fraction.

In performing the immunostaining analysis, the following steps were performed. After 40 hours of either mock, wild-type AcNPV, or AcNPV-Y4 infection, Sf9 cells were seeded on poly-L-lysine (Sigma) coated chamber slides (Miles Scientific) and incubated overnight. Slides were washed with phosphate-buffered saline between each of the following steps: cells were first fixed with 4% formaldehyde in 0.04 M phosphate buffer (pH 7.4) for 20 minutes or with acetone (−20° C.) for 10 minutes, and immersed in 1% $H_2O_2$ in methanol for 10 minutes. Fixed cells were preincubated with 2% normal goat serum in PBS for 10 minutes and then incubated overnight with rabbit anti-RB0.47 antibody diluted in 0.02% Triton X-100. After washing, biotinylated goat anti-rabbit IgG (TAGO, Burlingame, Calif.) was added. One hour later, cells were incubated with AB complex conjugated with horseradish peroxidase (Vector Labs, Burlingame, Calif.) for 45 minutes and then incubated with substrate. The substrate comprised 0.05% 3,3'-diaminobenzidine tetrahydrochloride and 0.01% $H_2O_2$ in 0.05 M Tris-HCl, pH 7.6 (Sigma). Reactions were stopped 3 to 5 minutes later by washing cells with PBS. Subsequently, the cells were photographed with a Nikon diaphotomicroscope.

Referring now to FIG. 4, there is shown the results of phosphorylation of RB protein produced in insect cells and dephosphorylation analysis. Forty hours after infection with AcNPV-Y4 RB, Sf9 cells were metabolically labelled with $^{35}$S-methionine or $^{32}$p-orthophosphate for 3 hours. Molt-4 was included as the control and cellular lysates were then immunoprecipitated with anti-RB0.47 antibody. The $^{35}$S- and $^{32}$P-labeled RB protein immune complexes were separated by SDS-PAGE before (lanes 1, 2, 3 and 4) or after treatment with potato acid phosphatase (PAP) (lanes 1', 2', 3' and 4') and analyzed by autoradiography. Similar dephosphorylation experiments using lysates from unlabeled cells were performed and subjected to Western blot analysis before and after treatment with potato acid phosphatase (lanes 5, 6 and 5', 6' respectively).

With further reference to FIG. 4, phosphorylation of RB protein occurs at multiple serine and threonine residues and accounts for the molecular weight heterogeneity of RB protein in the SDS-PAGE Oncogene Res., 1: 205–214, (1989) Cell, 56: 57–65, (1989). To determine whether RB protein produced in the insect cells undergoes phosphorylation post-translationally, AcNPV-Y4 RB-infected Sf9 cells were metabolically labeled with $^{35}$S-methionine or $^{32}$P-orthophosphate for 3 hours at 40 hours after infection. Cell extracts were subjected to immunoprecipitation and analyzed by SDS-PAGE followed by autoradiography. In this regard, please see FIG. 4, lanes 2 and 4, respectively. In parallel, immunoprecipitable RB protein from the same extracts was treated with potato acid phosphatase (PAP) to test the effect of dephosphorylation on RB protein mobility in SDS-PAGE. After dephosphorylation, the $^{35}$S-labeled RB protein was reduced from a doublet to a single band of Mr 110,000, (FIG. 4, lane 2'), and radioactivity was almost completely released from $^{32}$P-labeled RB protein (FIG. 4, lane 4'). Dephosphorylation analysis by Western blotting of lysates from unlabeled cells infected with AcNPV-Y4 RB also showed the same band reduction pattern after PAP treatment (FIG. 4, lanes 6 and 6'). These observations indicated that RB protein produced in insect cells was phosphorylated, and the modification also accounted for the molecular weight heterogeneity of this RB protein observed in the SDS-PAGE.

In performing the radiolabeling of Sf9 insect cells and dephosphorylation analysis, the following steps were performed. At 40 hours post-infection, Sf9 cells ($3 \times 10^6$) in 60 mm dishes were incubated with DME medium lacking either methionine or phosphate and supplemented with 10% fetal calf serum for 30 minutes. The cells were then metabolically radiolabeled by supplementing with 0.25 mCi/ml $^{35}$S-methionine (1134 Ci/mmole, NEN) or with 0.25 mCi/ml $^{32}$P-orthophosphate (carrier-free, ICN) for 3 hours. Cell extracts were then prepared in lysis buffer (50 mM Tris-HCl, pH 7.4; 0.2% Nonidet P-40; 1 mM EDTA; 100 mM NaCl; 50 mM NaF and 1 mM PMSF), and immunoprecipitation with anti-RB0.47 antibody was performed.

Two-thirds of the immunoprecipitated RB protein, from $^{35}$S or $^{32}$P-labeled as well as unlabeled cell lysates, were subjected to potato acid phosphatase (PAP, Boehringer) dephosphorylation analysis Oncogene Res., 1: 205–214, (1989). Immune complexes containing the RB protein were incubated with 1.5 units of PAP in reaction buffer (20 mM MES, pH 5.5; 100 mM NaCl; 1 mM MgCl$_2$; 50 $\mu$M leupeptin) for 60 minutes at 37° C. After the reaction, RB protein was analyzed by 7.5% SDS-PAGE, followed by either autoradiography or Western blotting.

B4. Purification of RB Protein from Infected Insect Cells

Sf9 cells were infected with AcNPV-Y4 RB at a multiplicity of infection (MOI) of 1.0, and forty hours after infection cellular lysates were prepared. Under this condition the total level of RB protein expressed in the baculovirus system was approximately 17–18 mg per liter of infected insect cell culture (~109 cells). In this regard, reference may be made to Table 1.

TABLE 1

Purification of recombinant RB protein from baculovirus infected insect cells.

| Step | Total protein (mg) | RB protein (mg) | Yield (%) | Purification fold | Purity (%) |
|---|---|---|---|---|---|
| Cellular Extract | 670[a] | 16[c] | 90[c] | 1.0 | 2.3 |
| pMG3-245 Immuno-affinity Column | 13.5[b] | 12.8[d] | 72[c,d] | 41.3 | 95 |

[a]Protein quantitation by the method of Bradford (Bio-RAD).
[b]Protein quantitation by Micro BCA (PIERCE) and spectrophotometry.
[c]Protein quantitation by Western blot and densitometry
[d]Protein quantitation by Coomassie brilliant blue staining and densitometry.

As shown in Table 1, 90% (16 mg) of the RB protein expressed were found in the supernatant after cell disruption, while 10% remained in the insoluble fraction. The RB protein could readily be detected in the cellular lysate (FIG. 5, lane 2) as it represented 2.3% of the total cellular protein. Following the one-step immunoaffinity chromatographic purification, approximately 13.5 mg of proteins could be recovered from the alkaline eluates of the column. To estimate the purity of the eluted RB protein, an aliquot of the eluates corresponding to $2.5 \times 10^5$ cells was analyzed by SDS-PAGE and Coomassie brilliant blue staining.

Figure 5:
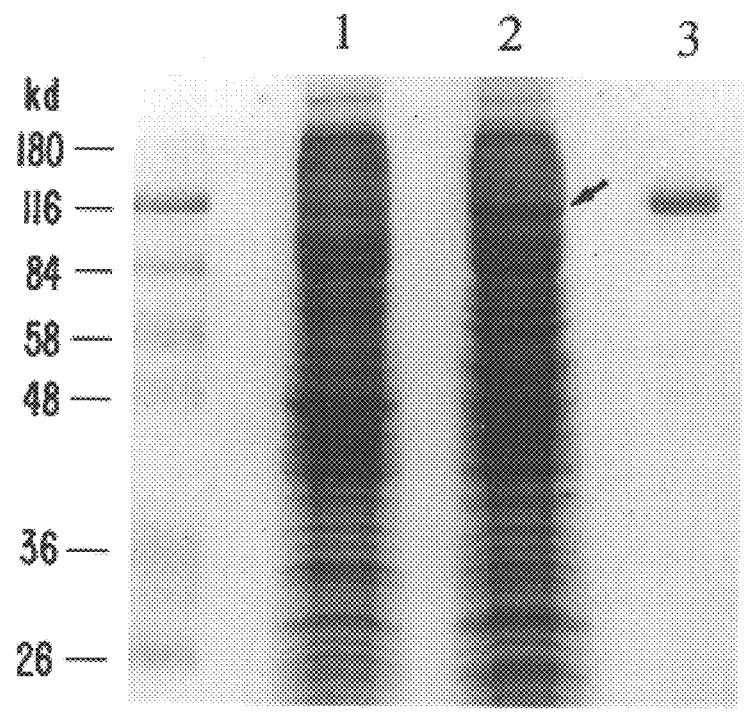
FIG. 5 depicts the electrophoretic analyses of crude lysates, infected Sf9 cells and eluates from pMG3-245 anti-RB.

In this regard, reference may be made to FIG. 5 which depicts immunoaffinity chromatographic purification of pp110$^{RB}$. Crude lysates from $1 \times 10^5$, mock- (lane 1) or AcNPV-Y4 RB-infected (lane 2) Sf9 cells as well as an aliquot (corresponding to $2.5 \times 10^5$ infected cells) of the eluates from the pMG3-245 anti-RB immunoaffinity chromatography (lane 3) were analyzed by electrophoresis on a 10% SDS-polyacrylamide gel, followed by Coomassie brilliant blue staining. The arrow indicates the position of the RB protein with the expected molecular weight.

As judged by densitometry, the single purification step described herein proved to be efficient, resulting in a preparation of RB protein with 95% purity (FIG. 5, lane 3), a 72% yield and a 41.3-fold of purification (Table 1).

Procedures for the construction of the immunoaffinity column followed the methods described by Schneider et al. and Simanis et al. with minor modification J. Biol. Chem., 257: 10766–10769, (1982) Virology, 144: 88–100, (1985). 2 ml of protein G-Agarose (Genex) were packed in a Bio-Rad column and washed with 0.01 N HCl followed by the binding buffer (0.1 M sodium acetate, pH 5.0; 0.1 M NaCl). 15 mg of anti-fRB monoclonal antibody (pMG3-245) were applied to the column twice to allow binding. The column was then washed extensively with 0.1 M borate buffer, pH 9.0, and the beads were resuspended in 20 ml of the buffer. Dimethylpimelimidate dihydrochloride (Sigma) was added to a final concentration of 40 mM, and the mixture was agitated for 1 hour at room temperature for the crosslinking reaction to take place. After washing, the remaining reactive groups of the beads were blocked with 40 mM ethanolamine-HCl in 20 ml of 0.1 M borate buffer, pH 8.0, for 10 minutes at room temperature. The column was then washed with 0.2 M glycine, pH 2.3 and neutralized with Tris buffer (50 mM Tris-HCl, pH 7.4; 100 mM NaCl; 1 mM PMSF; 1 mM EDTA) in which it was stored until required. By measuring OD$_{280}$ of the original monoclonal antibody sample, and that of the flow-through fractions in subsequent steps, it was estimated that approximately 10 mg of pMG3-245 were coupled to the 2 ml of protein G-Agarose beads.

B5. DNA-binding Activity and Specific Complex Formation With SV40 T Antigen

To date, two biochemical properties of the RB protein have been described. One is its ability to bind DNA intrinsically Nature, 329: 642–645, (1987), and the other is its ability to form specific complexes with oncoproteins of several DNA tumor viruses Cell, 54: 275–283, (1988); Science, 243: 934–937, (1989); Nature (London), 334: 124–129, (1988). The RB protein purified from baculovirus-infected insect cells was tested for these two known biochemical properties, which have been implicated in the biological functions of the protein.

Figure 6A:
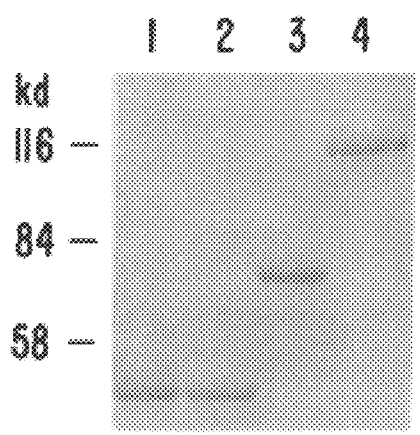
FIG. 6A depicts a Southwestern DNA binding assay of fusion proteins and baculovirus-expressed $pp110^{RB}$ applied to 10% SDS-PAGE, Coomassie brilliant blue staining.
Figure 6B:
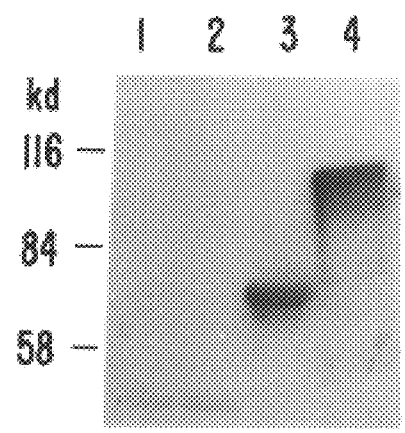
FIG. 6B is an autoradiograph of a blot from a parallel gel to the gel used to produce FIG. 6A, the blot having been incubated with $^{32}$P-labeled DNA fragments.

FIGS. 6A and 6B depict Southwestern DNA-binding assays. Six $\mu$g of purified trpE-RB fusion proteins, as well as the purified baculovirus-expressed pp110$^{RB}$, were applied to 10% SDS-PAGE. In the assay depicted in FIG. 6A, Coomassie brilliant blue staining was utilized while in the assay of FIG. 6B, a parallel gel was electrotransferred onto nitrocellulose paper. The blot was then incubated with $^{32}$P-labeled DNA fragments and analyzed by autoradiography. In FIGS. 6A and 6B, the following are shown: Lane 1: RB19-22; lane 2: RB23-27; lane 3: RB19-27; lane 4: purified RB protein from AcNPV-Y4 RB infected insect cells.

With regard to FIGS. 6A and 6B, DNA-binding was assayed by Southwestern analysis in which identical amounts of the trpE-RB fusion proteins, as well as the purified RB protein from insect cells, were separated by 10% SDS-PAGE. The quantity of loaded protein was confirmed by Coomassie brilliant blue staining (FIG. 6A). Another gel run in parallel was electrotransferred to a nitrocellulose membrane, followed by incubation with $^{32}$P-labeled DNA. DNA bound to the protein was then analyzed by autoradiography (FIG. 6B). It has been determined that fusion protein RB19-27, which contains the major domain for interacting with DNA, has a 20-fold higher affinity for DNA than either of two subregions, RB19-22 and RB23-27. In this regard, lane 3 of FIG. 6B can be compared with lanes 1 and 2, while the purified full-length RB protein exhibited a strong DNA-binding activity similar to that of RB 19-27 (FIG. 6B, lane 4). DNA-binding activity of the purified RB protein from insect cells was also demonstrated by retention of the protein by DNA-cellulose and its subsequent elution from the column, at approximately 400 mM NaCl.

In the purification of pp110RB from infected insect cells the following procedures were followed. Sf9 cells were infected with AcNPV-Y4 RB at a MOI of 1.0, and cultured in suspension (1×16$^6$ cells/ml, 1000 ml). After 40 hours of infection, the cells were pelleted by low-speed centrifugation, washed, and resuspended in an extraction buffer containing 50 mM Tris-HCl, pH 7.4; 0.2% NP-40; 1 mM EDTA; 100 mM NaCl; 10% (v/v) glycerol; 1 mM DTT; 1 mM PMSF; 25 µg/ml leupeptin and 50 units/ml aprotinin. After 15-minute incubation on ice, the sample was clarified by centrifugation (10,000×g, 4° C. for 10 minutes), and the RB-containing supernatant was collected. Immunoaffinity chromatography of pp110$^{RB}$ was carried out on a two-ml-volume column containing anti-fRB monoclonal antibody (pMG3-245) linked to protein G-Agarose as described above. After passing the supernatant through the column four times, the column was washed sequentially with 200 bed-volumes of each of the following: lysis buffer, lysis buffer containing 500 mM NaCl, and washing solution (200 mM NaCl; 1 mM EDTA; 1 mM DTT; 1 mM PMSF; 10% glycerol). Bound proteins were then eluted from the column by alkaline elution buffer containing 20 mM triethylamine, pH 10.8; 200 mM NaCl; 1 mM EDTA; 1 mM DTT; 1 mM PMSF and 10% glycerol. One-ml fractions were collected, immediately neutralized with one-twentieth volume of 1M Tris-HCl (pH 7.5), and stored at −70° C. in 10% glycerol.

In purifying the pp110$^{RB}$ from the infected insect cells, the amount of total protein was determined and, subsequently Southwestern DNA-binding assays and SV40 T antigen binding assays were performed.

The amount of total protein in the elution fraction of the immunoaffinity column was determined by Micro-BCA assay (PIERCE). The eluted protein sample was then analyzed by SDS-PAGE, and the amount of RB protein in the eluates was estimated by Coomassie brilliant blue staining followed by densitometry. The amount of total protein in the cellular extract was measured by the method of Bradford (Bio-Rad) *Anal. Biochem.*, 72: 248–254, (1976). To quantitate RB protein in cellular lysates, Western blotting was performed using serially diluted purified RB protein as standard followed by densitometric comparison of the band intensity. In this regard, reference may be made to Table 1.

Protein blotting was performed, utilizing conventional techniques. Incubation of blots with radiolabeled DNA followed the protocols described by Bowen et al. *Nucleic Acids Res.* 8: 1–21, (1980). The procedure was carried out at room temperature. Blots were rinsed briefly with water and then washed three times with 6M urea; 0.2% NP-40 (20 min each), followed by four washes (30 min each) with DNA-binding buffer (10 mM Tris-HCl, pH 7.0; 1 mM EDTA; 50 mM NaCl; 0.2% BSA; 0.2% Ficoll 400 and 0.2% polyvinyl pyrolidone). The blots were then incubated for 30 min in DNA-binding buffer containing $^{32}$P-labeled DNA. pGEM1 DNA linearized by EcoR1 was labeled with α-$^{32}$P deoxynucleotides (Amersham, >3000 Ci/mmol) by random priming and was used as the probe. After hybridization, blots were washed three times (10 min each) with DNA-binding buffer, air-dried, and analyzed by autoradiography. TroE-RB fusion proteins were included as controls. Each trpE-RB fusion protein was named according to the exons of the RB gene that the protein contains. Thus, RB19-22, RB23-27, and RB19-27 spanned the regions of pp110$^{RB}$ from exon 19 to 22 (amino acids 612–775), exon 23 to 27 (amino acid 776–928) and exon 19 to 27 (amino acid 612–928) respectively.

SV40 T antigen was purified by immunoaffinity chromatography from Ad-SV X1-infected 293 cells *J. Virol.*, 53: 1001–1004, (1985); Cold Spring Harbor Press. Cold Spring Harbor, N.Y. pp .187–192, (1982) and anti-T monoclonal PAB419 antibody was obtained from Oncogene Inc. A known complex formation assay was performed, with minor modification, in which 800 ng of baculovirus expressed RB protein was mixed with 1 ml of EBC buffer (50 mM Tris-HCl, pH 8.0, 120 mM NaCl and 0.5% Nonidet P-40) containing 1 mM PMSF, 25 µg/ml leupeptin and 50 units/ml aprotinin. 800 ng of purified T was added to the mix and mixture was incubated on ice for 90 minutes. Aliquots of the mixture were immunoprecipitated with either anti-RB0.47 or PAB 419 antibody and subjected to Western blotting analysis. Blots were sequentially reacted with pMG3-245 followed by PAB419. After incubating with alkaline phosphatase-conjugated goat anti-mouse IgG, the blots were developed with colorigenic substrates.

To test the ability of the purified RB protein in forming a specific complex with SV40 T antigen, equal amounts of RB protein and T antigen were mixed, and aliquots of the mixture were immunoprecipitated with either anti-RB0.47 antibody or anti-T antibody PAB419.

Figure 7:
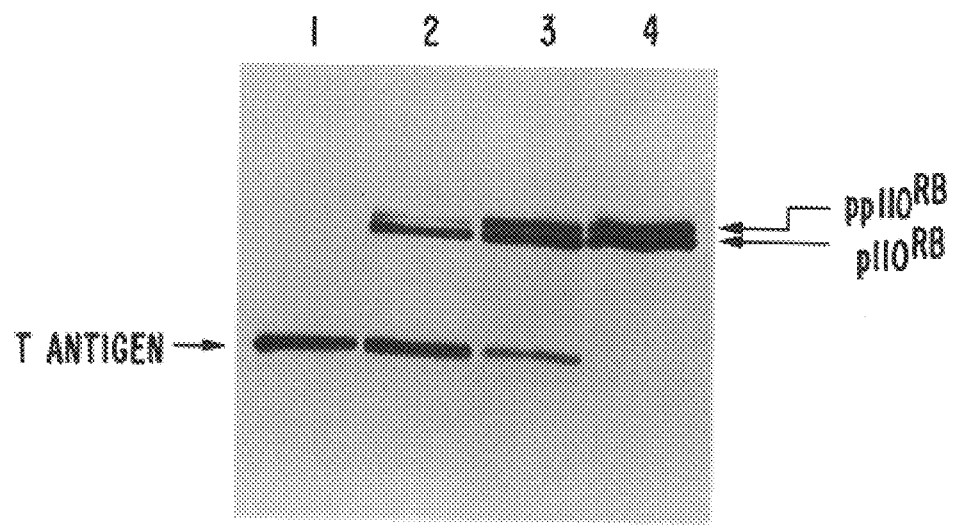
FIG. 7 is a chromatogram showing complex formation of baculovirus-expressed RB protein with SV40 T antigen.

In this regard, FIG. 7 depicts complex formation of baculovirus-expressed RB protein with SV40 T antigen. Purified baculovirus-expressed RB protein were mixed with purified T antigen in vitro. Identical aliquots of the mixtures were then immunoprecipiated with PAB419 (lane 2) or anti-RB0.47 (lane 3) and analyzed by Western blotting. Lanes 1 and 4 show purified SV40 T antigen immunoprecipiated with PAB419, and purified baculovirus-expressed RB protein immunoprecipitated with anti-RB0.47 antibody respectively.

As shown in FIG. 7, mixing of RB protein with T antigen in vitro resulted in the co-immunoprecipitation of RB protein with PAB419 (lane 2), as well as the co-immunoprecipitation of T with anti-RB0.47 antibody (lane 3). These data demonstrated that RB protein from baculovirus-infected insect cells are capable of forming a specific complex with SV40 T antigen.

B6. Nuclear Translocation of Purified RB Protein

After determining that the purified protein retained the two known biochemical activities of RB in vitro, the behavior of the purified protein in vivo, was investigated. Purified RB protein was injected into the cytoplasm of Saos-2 cells, an osteosarcoma cell line which contains a defective RB gene with deletion of exons 21-27 and encodes a C-terminal truncated RB protein (p95) *Proc. Natl. Acad. Sci. U.S.A.*, 87: 6–10, (1990). This protein is located in the cytoplasm in such minute amounts that it is not recognized by the anti-RB0.47 antibody used herein, in view of the fact that the antibody is directed against the C-terminus of RB protein.

Immediately after injection, cells were fixed and subjected to immunostaining analysis.

Figure 8:
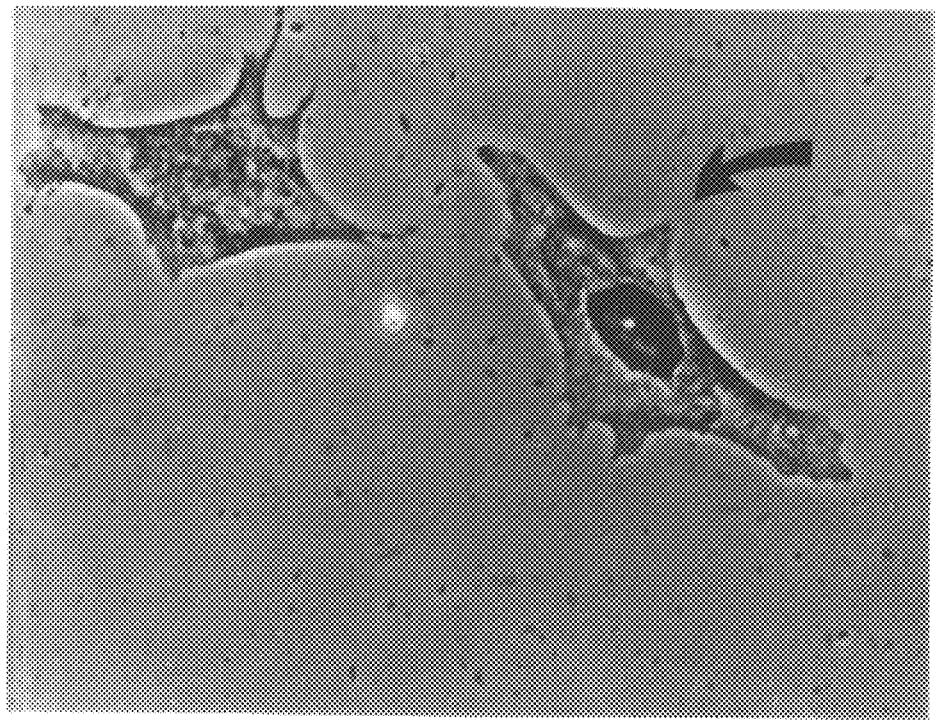
FIG. 8 is a photograph depicting nuclear translocation of purified RB protein after microinjection into the cytoplasm of Saos-2 cells.

FIG. 8 depicts nuclear translocation of the purified RB protein after microinjection into cytoplasms of Saos-2 cells. The cells were injected with purified RB protein and subjected to immunostaining analysis. The arrow indicates the intense staining of the nucleus after microinjection, as compared to that of uninjected cells.

As shown in FIG. 8, intense staining of the nucleus of the injected cell was found (arrow) as compared to that of the uninjected control, indicating the rapid transport of the injected protein into the nuclei. Since RB protein has been known as a nuclear protein, the prompt and accurate nuclear translocation of purified protein, after microinjection, further suggests that the protein is active in vivo.

For microinjection, purified RB protein was dialyzed into injection buffer containing 20 mM Tris-HCl, pH 7.4; 10 mM KCl; 0.1 mM EDTA; 0.1 mM DTT and 2% glycerol to a final concentration of 0.5 mg/ml. Saos-2 cells, growing on glass chamber slides were microinjected according to conventional techniques, using glass capillary needles (Eppendorf). An Eppendorf micromanipulator, equipped with a vacuum and pressure device, and an inverted phase-contrast microscope (Nikon) were employed for micromanipulation of the capillary and visualization of the microinjection process. After microinjection, the cells were immediately fixed by 4% formaldehyde in 0.04 M phosphate buffer (pH 7.4) and subjected to immunostaining analysis.

B7. Summary

As the foregoing has disclosed, it has been demonstrated that the human retinoblastoma gene product can be expressed efficiently under the transcriptional control of the baculoviral polyhedrin promoter. The attempt to express RB protein at high levels has long been regarded as difficult since it was suspected that RB protein might hinder or even be "toxic" to the growth of cells. The transcription of foreign genes from the polyhedrin promoter occurs late in infection, following production of extracellular viral particles and the shut-off of cellular and most viral genes. The baculovirus-insect cell system is therefore advantageous for the synthesis of proteins, such as the RB protein which may be detrimental to cell growth when overproduced. Another advantage of this system is the similarity in protein processing pathways of insect and mammalian cells.

The RB protein produced has been shown to be accurately targeted to the nuclei of insect cells, implying that mammalian nuclear translocation signals are also recognized by insect cells. Although glycosylation of recombinant proteins in the baculovirus expression system seems limited to the O-linked and N-linked oligosaccharides of the high mannose-type, appropriate phosphorylation of foreign proteins has been reported for the expression of c-myc and HTLV-I p40$^x$ J. Virol. RB protein has previously been shown to be phosphorylated but not glycosylated, making the baculovirus expression system suitable for the production of functional RB protein.

As disclosed herein, the RB protein produced in infected insect cells is post-translationally phosphorylated, and multiple bands can be differentiated by Western blotting analysis, just as in the case of authentic mammalian RB protein. However, as judged by band intensity, un- and hypophosphorylated forms are predominant when compared to the hyperphosphorylated RB protein. At present, it is not known whether this phenomenon is a reflection of the cell cycle status of the population, during a viral lytic infection, or is simply due to the insufficient phosphorylation of the protein by insect kinases because of the massive amount of exogenous RB present in the cells. Precise mapping of phosphorylation sites in the RB protein will be necessary in order to determine whether the phosphorylation patterns are truly identical to that of mammalian protein.

The total level of recombinant RB protein expressed in the baculovirus system is about 17–18 mg per liter of infected insect cell culture (~$10^9$ cells). This level of expression is comparable to other mammalian proteins produced by this system, such as 10–20 mg/l for interleukin 2 *The Banbury Report*. Fields, B., Martin, M. A. and Kamley, D. (ed.), 22: 319–328, (1985) Cold Spring Harbor Laboratory Press, Cold Spring Harbor, and 4–5 mg/l for P210 BCR-ABL *Oncogene*, 4: 759–766, (1989). The high level of expression of RB protein may be enhanced by using a recombinant transfer vector containing the intact polyhedrin 5' untranslated region, fused with the RB cDNA deprived of most of its 5' non-coding region. This sequence of the RB mRNA is highly G+C rich, a factor which may favor the formation of stable secondary structures. These structures, when present in front of an initiation codon, are thought to decrease the translational efficiency of the corresponding mRNA. Five-to ten-fold enhancement of the in vitro translation of RB mRNA has been demonstrated by the replacement of RB 5' untranslated sequence with that of the alfalfa mosaic virus (AMV) RNA4, or β-globin mRNA, further suggesting the potential adverse effect, on the translation, *EMBO J.*, (in press), (1990) of RB 5' non-coding sequence. The presence of long 5' untranslated sequences of the foreign genes has also been shown to affect the recombinant protein expression in the baculovirus system. Since the polyhedrin promoter is very A+T-rich, it has been concluded that the long and G+C-rich 5' non-coding sequence be trimmed from the RB cDNA, prior to the insertion into the transfer vector, for optimal expression of pp110$^{RB}$.

Several different protocols for the elution of RB protein from affinity columns have been tested in an attempt to minimize the denaturation of protein during the purification process. Since not much is known of the biological functions and biochemical properties of RB protein, the only two parameters that can be used as measures of the integrity of purified protein are the activities of DNA-binding and complex formation with SV40 T antigen. It was found that the present elution condition, using 20 mM triethylamine at pH 10.8 was effective in preserving the biochemical properties of the protein. Rapid nuclear translocation of the purified protein from the cytoplasm after microinjection further demonstrated that the protein was active under this elution condition. Elution of the protein at extreme pH (200 mM glycine, pH 2.3 or 100 mM triethylamine, pH 11.5) tended to denature the protein in that the aforementioned two activities were greatly diminished. This was also made evident by the formation of insoluble aggregates, after long term storage.

While it has been previously reported that only the unphosphorylated RB protein can bind SV40 T antigen in D2C2 cells, a stable transformant of monkey kidney cell line CV1-P by SV40 T antigen *Cell*, 56: 57–65, (1989), it was found that certain hypophosphorylated forms of the RB protein were able to form complexes with the SV40 T antigen. This was reproducibly demonstrated with the in vitro mixing of T antigen with purified RB protein from AcNPV-Y4 RB infected-insect cells, or with Molt-4 lysates. The same phenomenon has been observed when Cos cells for in vivo complex formation were used (FIG. 7). Since phosphorylation of the RB protein oscillated during the cell cycle in a phase-specific manner and the complex formation between RB and viral oncoproteins has been implicated in the transforming activity of these DNA tumor viruses, the significance of the association between hypophosphorylated RB protein and SV40 T antigen awaits future elucidation.

The availability of significant amounts of soluble, intact and presumably active RB protein, utilizing the baculovirus-insect cell system represents a major advance for future studies of the biochemical and biophysical properties of the RB gene product. Possible applications include analyses of associated cellular proteins, isolation of the specific DNA sequence with which they interact, and three-dimensional structural studies of the RB protein utilizing X-ray crystallography. The elucidation of the biological function of the retinoblastoma gene in cancer suppression can also be facilitated. The possible involvement of RB in cell growth and differentiation, directly tested by microinjection, are now under active investigation.

Some of the abbreviations used in this specification are: cDNA, complementary DNA; kd, kilodalton; kb, kilobase; SDS, sodium dodecyl sulfate; PAGE, polyacrylamide gel electrophoresis; NP-40, Nonidet P-40; MES, (2-[N-Morpholino]ethanesulfonic acid) sodium salt; MOI, multiplicity of infection; Mr, relative molecular mass; PAP, potato acid phosphatase. The protein product, identified herein as "pp110$^{RB}$" is the same protein product identified elsewhere as "ppRB$^{110}$."

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A baculoviral expression vector capable of expressing a soluble human retinoblastoma polypeptide in a host cell wherein said expression vector is an *Autographa californica* nuclear polyhedrosis baculovirus genome comprising DNA encoding the soluble human retinoblastoma polypeptide under the transcriptional control of a polyhedrin promoter.

2. A *Spodoptera frugiperda* host cell transfected with the baculoviral expression vector of claim 1.

3. Soluble retinoblastoma polypeptide expressed by the baculoviral expression vector of claim 1 wherein the host cell is *Spodoptera frugiperda*.

4. A method for producing purified soluble human retinoblastoma polypeptide comprising:
   a. inserting a DNA molecule encoding soluble human retinoblastoma polypeptide into an *Autographa californica* nuclear polyhedrosis baculoviral expression vector wherein said DNA is under the transcriptional control of a polyhedrin promoter;
   b. inserting the resulting vector into a *Spodoptera frugiperda* insect host cell;
   c. culturing said host cell under conditions to express the soluble human retinoblastoma polypeptide; and
   d. purifying said resulting soluble human retinoblastoma polypeptide so produced.

5. The purified soluble retinoblastoma polypeptide of claim 3, wherein the soluble polypeptide is purified and isolated human retinoblastoma $pp110^{RB}$, substantially free of other human proteins.

6. The method of claim 4, wherein said DNA has deleted from the 5' non-coding region the G+C rich region from about nucleotide +1 to about nucleotide +115 and wherein said DNA has the sequence of SEQ ID No. 1.

7. The expression vector of claim 1, wherein said DNA has deleted from the 5' non-coding region the G+C rich region from about nucleotide +1 to about nucleotide +115 and wherein said DNA has the sequence of SEQ ID No. 1.

* * * * *